US011707372B2

(12) United States Patent
Risch

(10) Patent No.: US 11,707,372 B2
(45) Date of Patent: Jul. 25, 2023

(54) PROCESS FOR MACHINE PRE-CRIMPING OF STENTS, ESPECIALLY DRUG-COATED STENTS

(71) Applicant: BIOTRONIK AG, Bülach (CH)

(72) Inventor: Fabian Risch, Doerflingen (CH)

(73) Assignee: BIOTRONIK AG, Buelach (CH)

( * ) Notice: Subject to any disclaimer, the term of this patent is extended or adjusted under 35 U.S.C. 154(b) by 192 days.

(21) Appl. No.: 17/293,301

(22) PCT Filed: Nov. 19, 2019

(86) PCT No.: PCT/EP2019/081775
§ 371 (c)(1),
(2) Date: May 12, 2021

(87) PCT Pub. No.: WO2020/109075
PCT Pub. Date: Jun. 4, 2020

(65) Prior Publication Data
US 2022/0008235 A1    Jan. 13, 2022

(30) Foreign Application Priority Data
Nov. 27, 2018 (DE) .......................... 102018129917.6

(51) Int. Cl.
*A61F 2/95* (2013.01)
*A61F 2/958* (2013.01)

(52) U.S. Cl.
CPC ............ *A61F 2/9524* (2020.05); *A61F 2/958* (2013.01); *A61F 2240/001* (2013.01); *A61F 2250/0067* (2013.01)

(58) Field of Classification Search
CPC ...... A61F 2/9524; A61F 2/958; A61F 2/9522; A61F 2240/001; A61F 2250/0067; A61M 2025/1081
See application file for complete search history.

(56) References Cited

U.S. PATENT DOCUMENTS

| 7,765,670 | B2* | 8/2010 | Spencer | ................ | A61F 2/9524 |
| | | | | | 29/451 |
| 2005/0159802 | A1* | 7/2005 | Furst | ....................... | A61F 2/958 |
| | | | | | 623/1.11 |
| 2006/0036310 | A1* | 2/2006 | Spencer | .................. | A61F 2/966 |
| | | | | | 623/1.12 |
| 2012/0324696 | A1* | 12/2012 | Liu | ........................... | A61F 2/97 |
| | | | | | 604/103.05 |
| 2014/0260097 | A1* | 9/2014 | Avery | ................... | A61F 2/9524 |
| | | | | | 72/367.1 |

OTHER PUBLICATIONS

International Search Report and Written Opinion from the corresponding International Patent Application No. PCT/EP2019/081775, dated Feb. 7, 2020.

* cited by examiner

*Primary Examiner* — Bayan Salone
(74) *Attorney, Agent, or Firm* — Greer, Burns & Crain, Ltd.; Steven P. Fallon

(57) ABSTRACT

A process for arranging a stent, especially a drug-coated stent, on a balloon of a balloon catheter. At a stent implantation site (e.g., during an angioplasty procedure), the balloon of the balloon catheter serves to expand the stent radially, so that the stent, e.g., opens a vascular stenosis and is securely fixed to the vessel wall. Pressure plates are arranged and operate to maintain a protection device that avoids contamination of the stent.

15 Claims, 26 Drawing Sheets

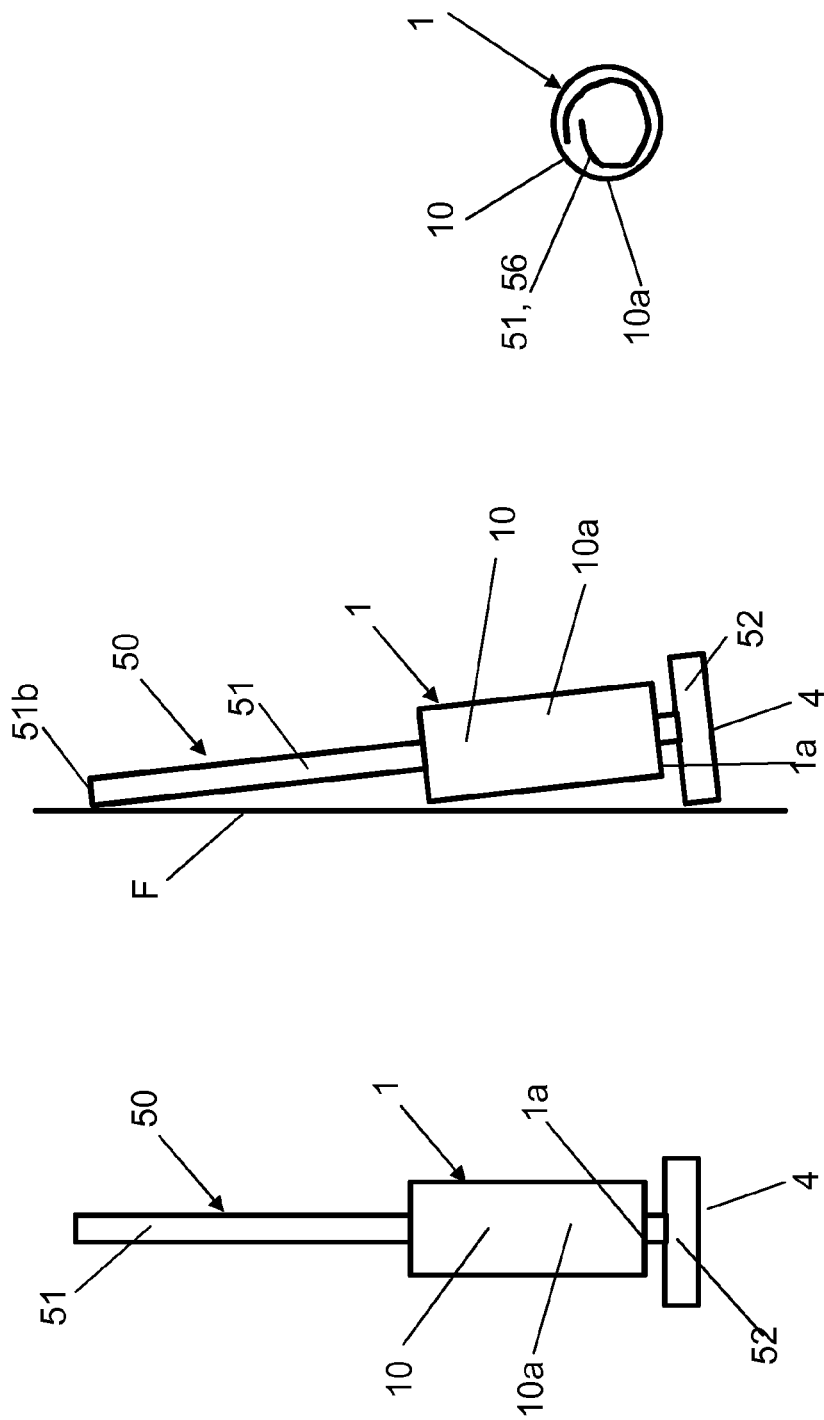

US 11,707,372 B2

PROCESS FOR MACHINE PRE-CRIMPING OF STENTS, ESPECIALLY DRUG-COATED STENTS

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/081775, which was filed Nov. 19, 2019, which application claimed priority from German Application Serial Number 10 2018 129 917, which was filed Nov. 27, 2018.

FIELD OF THE INVENTION

This invention relates to a process for arranging a stent, especially a drug-coated stent, on a balloon of a balloon catheter.

BACKGROUND

At a stent implantation site (e.g., during an angioplasty procedure), the balloon of the balloon catheter serves to expand the stent radially, so that the stent, e.g., opens a vascular stenosis and is securely fixed to the vessel wall.

In automated systems for producing such stent systems, it is advantageous to transport the stent between individual process steps by machine. E.g., from a stent magazine to a process step in which the stent is arranged or assembled on the balloon catheter.

This can be done, on the one hand, by mechanical grippers, or by exploiting gravity in a slide system, or by exploiting other forces, such as, e.g., magnetic forces or deflections due to compressed air, etc.

In all cases it is necessary to prevent cross contamination of the stents, especially drug-coated stents (i.e., stents that are coated with at least one drug), both during transport and also during assembly on the balloon catheter. This can be ensured, e.g., by cleaning the assembly system or the transport system after every individual product run, by replacing contaminated components, or by avoiding direct contact points.

However, in an automated system that processes large numbers of items, the first two methods mentioned (cleaning the assembly system or the transport system or replacing contaminated components) are very elaborate and cost-intensive to realize.

US2002/0116045 discloses a protective sheath for a catheter arrangement with a tubular element. U.S. Pat. No. 6,152,944 further discloses a removable stent protection device comprising a first removable sleeve that has a variable inside diameter to facilitate the sliding of the first sleeve over the balloon and the stent, the stent protection device being removed before the use of the stent delivery system. U.S. Pat. No. 8,003,157 further describes a system for coating a stent, with a device for weighing the stent, a device for aligning the stent with a stent support, and a device for coating the stent, and also a device for drying the stent and inspecting the stent. Finally, U.S. Pat. No. 8,430,057 discloses a chuck that is shaped to minimize the contact surface of a stent end.

SUMMARY OF THE INVENTION

A preferred process for arranging a stent on a balloon of a balloon catheter, includes:

a) Providing a stent having a wall structure that circles in a peripheral direction and that extends along a longitudinal axis and surrounds an interior of the stent extending along the longitudinal axis, the wall structure having an inner surface facing the interior and an outer surface facing away from the inner surface;

b) Providing a protection device to avoid contamination of the stent;

c) Inserting the stent in an insertion direction into an area between multiple movable pressure plates so that a stop limits motion of the stent in the insertion direction;

d) Moving the pressure plates in the direction toward the outer surface of the stent so that the stent is held by the pressure plates;

e) Inserting the balloon catheter into the interior of the stent so that the wall structure of the stent surrounds the balloon;

f) Moving the pressure plates in the direction toward the outer surface of the wall structure of the stent so that the pressure plates crimp the stent on the balloon; and g) Opening the pressure plates and withdrawing the balloon catheter out of the area between the pressure plates with the stent crimped on the balloon; wherein the stent is inserted into the area according to step c) such that one or both of the following occurs at least a first part of the protection device prevents contact between a face of the stent and the stop;

and at least a second part of the protection device is located between the outer surface of the wall structure of the stent and the pressure plates when the pressure plates are pressed against the outer surface of the stent with the second part of the protection device between them, the stent being held by the pressure plates in step d) with the second part of the protection device between them, and the pressure plates crimping the stent on the balloon in step f) with the second part of the protection device between them.

BRIEF DESCRIPTION OF THE DRAWINGS

The discussion below is intended to explain embodiments and features and advantages of this invention on the basis of the figures. The figures are as follows:

FIG. 24-25 another embodiment of the support;

FIG. 26 another embodiment of the support;

DETAILED DESCRIPTION OF THE PREFERRED EMBODIMENTS

Figure 1:
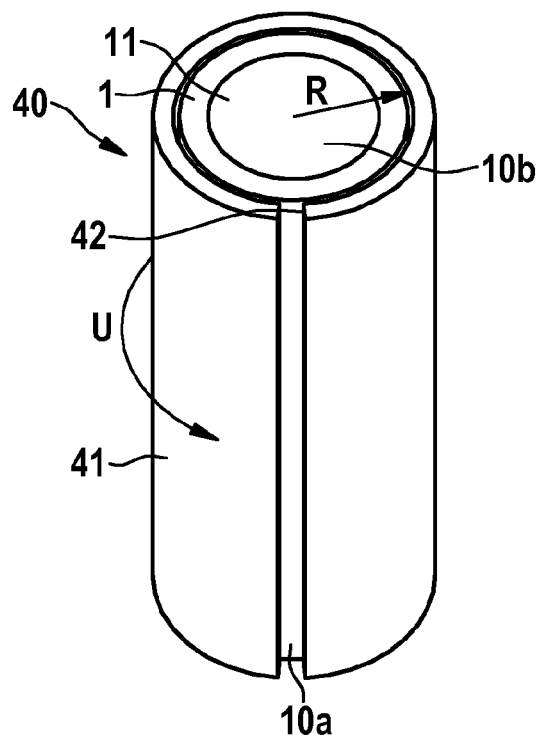
FIG. 1 a perspective view of a stent that is arranged in a protection device in the form of a capsule.

A process for arranging a stent on a balloon of a balloon catheter, includes:

a) Providing a stent having a wall structure that circles in a peripheral direction and that extends along a longitudinal axis and surrounds an interior of the stent extending along the longitudinal axis, the wall structure having an inner surface facing the interior and an outer surface facing away from the inner surface;

b) Providing a protection device to avoid contamination of the stent;

c) Inserting the stent in an insertion direction into an area between multiple movable pressure plates so that a stop limits motion of the stent in the insertion direction;

d) Moving the pressure plates in the direction toward the outer surface of the stent so that the stent is held by the pressure plates;

e) Inserting the balloon catheter into the interior of the stent so that the wall structure of the stent surrounds the balloon;

f) Moving the pressure plates in the direction toward the outer surface of the wall structure of the stent so that the pressure plates crimp the stent on the balloon; and g) Opening the pressure plates and withdrawing the balloon catheter out of the area between the pressure plates with the stent crimped on the balloon; wherein the stent is inserted into the area according to step c) such that one or both of the following occurs at least a first part of the protection device prevents contact between a face of the stent and the stop; and at least a second part of the protection device is located between the outer surface of the wall structure of the stent and the pressure plates when the pressure plates are pressed against the outer surface of the stent with the second part of the protection device between them, the stent being held by the pressure plates in step d) with the second part of the protection device between them, and the pressure plates crimping the stent on the balloon in step f) with the second part of the protection device between them.

The stop in step c) can be a withdrawable stop, so that in step d) the stop can still be withdrawn (if the stent is held by the pressure plates).

In one embodiment, the stop further has a hole, through which the balloon catheter can be pushed. In this case, the stop need not be withdrawn. Furthermore, in this case, the stop can also be integrated into the pressure plates.

For the case in which only the first part or only the second part of the protection device is used, making a distinction between a first part and a second part of the protection device is, of course, not applicable. The reason why is that then there is at least one part of the protection device that prevents contact between the face and stop, or there is at least one part of the protection device that is located between the outer surface of the wall structure of the stent and the pressure plates.

The stent is especially a drug-coated stent, so avoiding cross contamination of the stent is of great importance.

A preferred embodiment of the process provides that the pressure plates can be moved in the horizontal direction, the insertion direction preferably pointing vertically downward.

One embodiment of the process further provides that the stent be arranged, especially by the force of gravity, in the aforementioned area between the pressure plates so that the longitudinal axis of the stent runs vertically and the stent is supported, through the first part of the protection device, on the stop which is arranged vertically beneath the stent. Following the vertical approach of the embodiment upon bernefitting from gravity has also the advantage that devices could be used that are configured to expand vertically. Hence, such devices use the space in room expanding to the ceiling which is very efficient in times when space in buildings is very expensive.

One embodiment of the process further provides that the protection device or the first and the second parts of the protection device be formed by a capsule, which has at least one elastically deformable wall, the stent being arranged in the capsule before being arranged in the aforementioned area (between the pressure plates), so that the at least one wall surrounds at least sections of the outer surface of the wall structure of the stent (in particular, surrounds the outer surface of the wall structure of the stent except for a gap). It is particularly advantageous when the capsule is formed from an elastic material, because one the one hand the elastic material is capable of holding the stent in pace by tightening it to the catheter. One the other hand, the capsule will broaden again after the crimping facilitating the release of the crimped stent on the catheter from the capsule. In that, the capsule can be formed of any suitable elastic material ranging from polymer based material to metals. Also, capsules based on carbon fibres could be used. Related materials such as aero graphite or aero graphen could also be suitable as capsule material.

In particular, this involves arranging the capsule along with the stent in the aforementioned area between the pressure plates so that the capsule contacts the stop and the face of the stent is spaced apart from the stop.

One embodiment of the process further provides that the wall have a continuous gap extending in the axial direction, this gap allowing or simplifying compression of the wall in the radial direction. An alternative embodiment provides that the wall have two edges that overlap one another in the peripheral direction. This allows the edges to be moved against one another when the wall of the capsule undergoes radial compression or deformation.

Another embodiment of the process provides that the capsule have another wall that surrounds the at least one wall, especially in the peripheral direction. According to one embodiment, the other wall can also have a gap extending in the axial direction, the walls being arranged with respect to one another so that each wall covers the gap of the other wall.

According to one embodiment of the invention, the capsule or the at least one wall of the capsule is fixable or fixed to the stent, e.g., in a non-positive and/or positive manner, if the capsule together with the stent is arranged in the area between the pressure plates.

One embodiment of the process further provides that the capsule have, at one (e.g., lower) end, a projection, especially in the form of an open ring-shaped projection.

For the case in which the stent is inserted into the aforementioned area between the pressure plates in a vertical downward insertion direction, the projection is provided at a lower end of the wall.

One embodiment of the process further provides that the projection extend in a peripheral direction along an edge, especially a lower edge, of the at least one wall (or of the other wall), in particular being interrupted only by the gap of the at least one wall.

One embodiment of the process further provides that as the balloon catheter is withdrawn from the aforementioned area between the pressure plates, the projection form an abutment for at least one of the pressure plates or for all pressure plates, so that the capsule is not withdrawn from the aforementioned area between the pressure plates along with the balloon catheter, but rather remains in the aforementioned area, because the projection reaches behind, e.g., the bottoms of the pressure plates.

The empty capsule can then be removed from the area between the pressure plates when the pressure plates are reopened, in particular following gravity downward.

One embodiment of the process further provides that the first part of the protection device be formed by a support for the stent, the support having a pin that is inserted into the interior of the stent before the stent is arranged in the aforementioned area between the pressure plates. That is, the stent is inserted, in particular along with support, into the aforementioned area between the pressure plates so that the support makes contact with the stop, that is, so that the stent is supported against the stop through the support (in particular through the base of the support).

s One embodiment of the process further provides that the support have a base from which the pin sticks out and that the base project in the radial direction beyond the outer surface of the wall structure of the stent when the pin is inserted into the interior of the stent, in particular the stent being inserted, together with the support, into the aforementioned area in such a way that the base makes contact with the stop, in particular the stent being supported against the stop through the base.

One embodiment of the process further provides that an end section of the pin connected with the base be conically shaped to clamp the stent.

One embodiment of the process further provides that the support have a head part that is detachably connectable with the pin and/or with the base, this head part being connected with the pin and/or with the base before the stent is arranged in the aforementioned area. The head part preferably projects in the radial direction beyond the outer surface of the wall structure of the stent. Furthermore, the head part can be designed so that it forms a protective sheath surrounding the outer surface of the stent. One embodiment further provides that the head part be removed from the pin after insertion of the stent into the aforementioned area.

One alternative embodiment of the process further provides that the pin project out of the interior of the stent far enough that the stent cannot make contact with a planar surface if the base and one end of the pin lie on the surface. That is, here contact of the stent with a transport system (having, in particular, one or more slides) or with another adjacent wall is prevented solely by the base and the longitudinal extension of the pin of the support, so that it is possible to do without an additional head part of the support.

One embodiment of the process further provides that the pin have a spring element at an end section opposite the base. This allows the stent to be secured on the pin by means of the spring element, without a head part having to be connected with the pin. An advantage of having a spring element resides in that stents of different sizes can be processed without adapting the pin specifically to one sort of stent.

One embodiment of the process further provides that the pin have a first end section and an opposite second end section, the support further having a first and a second spring element, the first spring element being arranged on the first end section and the second spring element being arranged on the second end section of the pin. In such an embodiment, one of the spring elements can be compressed in the radial direction to push the stent onto the pin, advantageously making it possible to do without, e.g., a detachable head part of the support.

One embodiment of the process further provides that the pin for clamping the stent be in the form of a torsion spring or have a torsion spring, the pin being fixed to the stent by means of the torsion spring if the pin is inserted into the stent.

One embodiment of the process further provides that the second part of the protection device have one or more flexible film sheet(s), each of which can consist of or have, e.g., PTFE.

One embodiment of the process further provides that the one or more film sheet(s) be guided through the aforementioned area between the pressure plates so that the one or more film sheet(s) form a film tunnel enclosing the outer surface of the wall structure in the peripheral direction of the wall structure, in particular when the pressure plates are moved in the direction toward the outer surface of the wall structure of the stent. Such embodiment is advantageous when the stent be arranged by the force of gravity so that the longitudinal axis of the stent runs vertically. In combination with such an embodiment the film tunnel does not only provides protection, but also guidance in sense of a channel or guide conduct.

One embodiment of the process provides that the film sheet be unwound from a feed roller and be guided by means of multiple guide rollers to produce film sections that are opposite one another, and that the film sheet be wound up onto a take-up roller. The take-up roller can be driven to unwind the film sheet. Alternatively, it is also conceivable for the unwinding of the film sheet to be caused by the pressure plates.

For the case in which multiple separate film sheets are used, the respective film sheet is unwound from a feed roller and wound up onto a take-up roller. The respective take-up roller can be driven to unwind the respective film sheet. Alternatively, it is also conceivable for the unwinding of the respective film sheet to be caused by the pressure plates.

One embodiment of the process provides that the stop be in the form of a plunger that is inserted into the aforementioned area between the pressure plates, to limit a motion of the stent in the insertion direction, the stop being deformed in the radial direction by the pressure plates when the pressure plates are moved in the direction toward the outer surface of the wall structure of the stent.

One embodiment of the process further provides that the film sheet(s) be arranged so that they project beyond the pressure plates in the insertion direction.

One embodiment of the process further provides that the stent be arranged in the aforementioned area so that an end section of the stent projects beyond the pressure plates and/or beyond the at least one film sheet in the insertion direction, e.g., downward, for the case in which the insertion direction points vertically downward.

One embodiment of the process further provides that the first part of the protection device have a film sheet or be formed by a film sheet.

One embodiment of the process provides that this film sheet that is used to cover the stop be unwound from a feed roller and wound up onto a take-up roller. The take-up roller can be driven to unwind the film sheet. Alternatively, it is also conceivable for the unwinding of the film sheet from the feed roller to be caused by a movement of the stop.

One embodiment of the process further provides that the stent be repositioned with respect to the balloon after crimping on the balloon and, after the repositioning, that it be further crimped onto the balloon, to fix the repositioned stent on the balloon in a final manner, i.e., ready for implantation.

In other words, the first crimping is preferably a pre-crimping of the stent, so that the stent sits tightly on the balloon, however is still movable with respect to the balloon. The pre-crimped stent is then repositioned, to align the stent exactly with respect to the balloon. Then, the stent is crimped on the balloon of the balloon catheter in a final manner.

Finally, it should be noted with respect to this invention that in principle every one of the protection devices described here can also be used alone. For instance it is possible:

i) to use only the capsule;
ii) to use only the support (e.g., if a cross contamination can be excluded due to sufficiently small forces of the pressure plates), in which case the support only serves, e.g., as a protection device for transport to the pre-crimping head or to the pressure plates;
iii) to use only the film tunnel (if cross contamination of the stop can be excluded due to the small forces).

Figure 2:
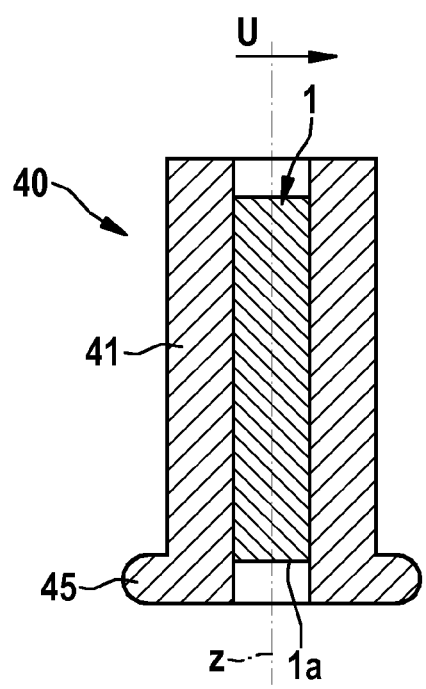
FIG. 2 a sectional view of the capsule shown in FIG. 1 with a stent arranged in it.
Figure 4:
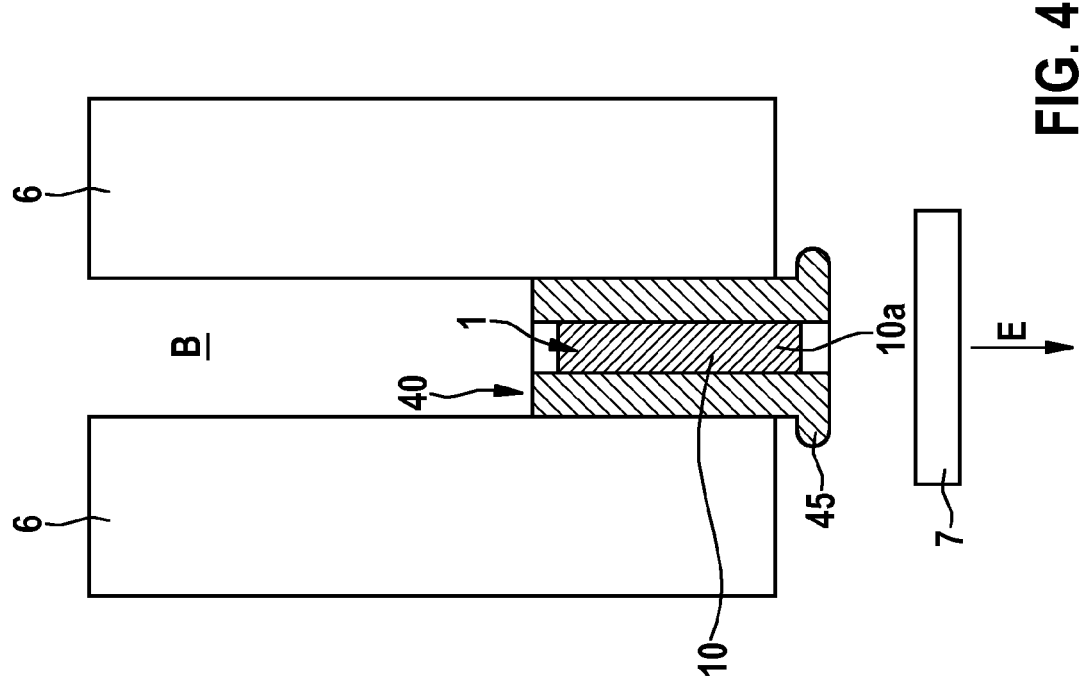
FIG. 3-8 crimping or pre-crimping the stent on a balloon of a balloon catheter using the protection device according to FIGS. 1 and 2.

This invention relates to a process for arranging or pre-crimping a stent 1 on a balloon 20 of a balloon catheter 2, wherein a preferably drug-coated stent 1 that has a wall structure (formed, e.g., from multiple struts that are integrally connected with one another) circling in a peripheral direction U, this wall structure extending along a longitudinal axis z and surrounding an interior 11 of the stent 1, this interior 11 extending along the longitudinal axis z (and later carrying the flow of blood), and this wall structure 10 having an inner surface 10b facing the interior 11 and an outer surface 10a facing away from the inner surface 10b (see, e.g., FIGS. 1 and 2). Furthermore, the process as is shown in FIGS. 3 through 8 or 14 through 19 or 22 through 23 or 29 through 40 uses a protection device 4, 5 to avoid contamination of the stent 1. This process involves inserting the stent 1 in an insertion direction E into an area B between multiple movable pressure plates 6 of a crimping tool, which is also called a crimping head, a withdrawable stop 7 limiting motion of the stent 1 in the insertion direction E and a first part 4 of the protection device preventing contact between a face 1a of the stent 1 and the stop 7, the insertion furthermore being done in such a way that a second part 5 of the protection device is located between the outer surface 10a of the wall structure 10 of the stent 1 and the pressure plates 6 when the pressure plates 6 are pressed against the outer surface 10a of the stent 1 with the second part 5 of the protection device 4, 5 between them. To crimp or pre-crimp the stent 1 on the balloon 20, the pressure plates 6 are moved in the direction toward the outer surface 10a of the wall structure 10 of the stent 1 (e.g., in the horizontal direction V), so that the stent 1 is held by the pressure plates 6 with the second part 5 of the protection device between them. In order that the balloon catheter 2 can now be inserted into the interior 11 of the stent 1, the stop 7 is then withdrawn (e.g., in the insertion direction E). When the stop 7 has been withdrawn, the balloon catheter 2 is inserted into the interior 11 of the stent 1, so that the wall structure 10 of the stent 1 surrounds the balloon 20 of the balloon catheter 2. Moving the pressure plates 6 in the direction toward the outer surface 10a of the wall structure 10 of the stent 1 in such a way that the pressure plates 6 press against the stent 1, with the second part 5 of the protection device between them, crimps the stent 1 on the balloon 20 (the inner surface of the wall structure coming to lie against the an outer surface of the balloon 20). This crimping is, in particular, a pre-crimping. That is, after this the stent 1 is still repositionable with respect to the balloon 20, the stent 1 only undergoing final fixation on the balloon 20 after that by (further) crimping the stent 1 again. After the crimping or pre-crimping, the pressure plates 6 are reopened, i.e., removed from the outer surface 10a of the wall structure 10 of the stent 2, and the balloon catheter 2 is withdrawn (e.g., in the direction opposite the insertion direction E) from the area B between the pressure plates 6.

The process involves the stent 1 being arranged, preferably by the force of gravity, in the aforementioned area B so that the longitudinal axis z of the stent 1 runs vertically and the stent 1 is supported, through the first part 4 of the protection device, on the stop 7 which is arranged vertically beneath the stent 1.

The embodiment shown in FIGS. 1 through 8 provides that the stent 1 be surrounded, in a preparatory step, by a capsule 40 that is preferably deformable in the radial direction R, this capsule 40 forming the first and second part of the aforementioned protection device. The capsule 40 is, in particular, robust enough to absorb transport- and process-related forces. The stent 1 is preferably held in the capsule 40 in a non-positive or positive manner.

Figure 3:
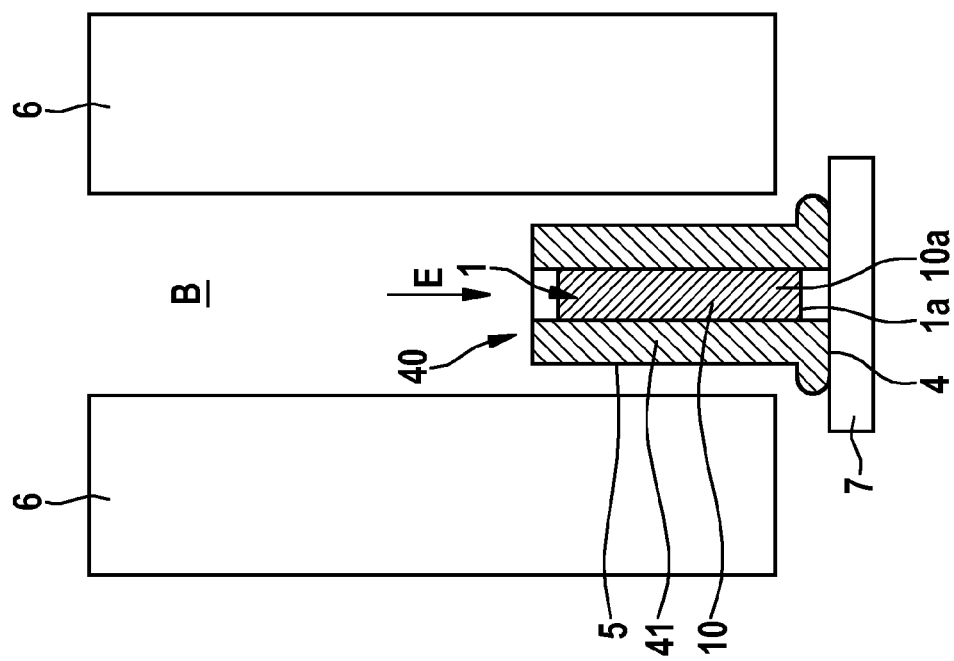
Figure 6:
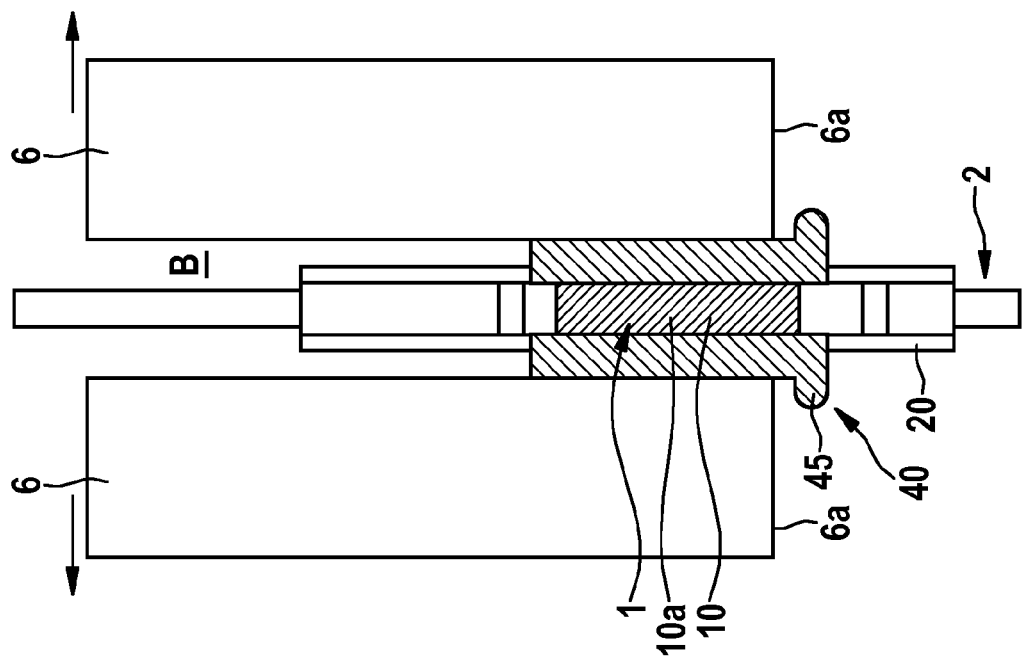
Figure 5:
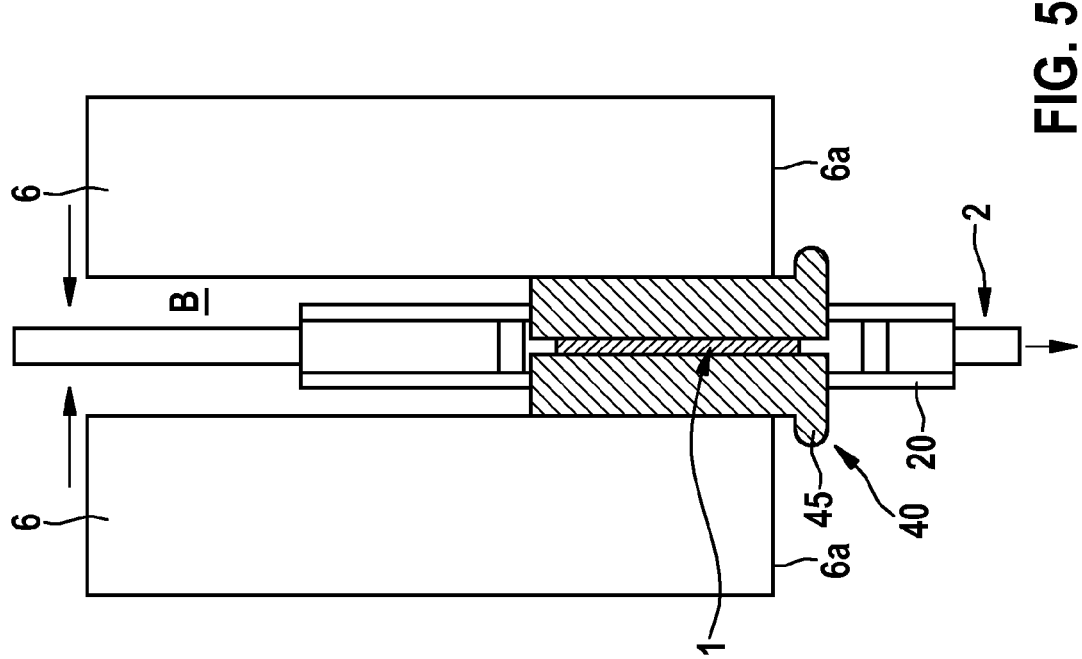
Figure 7:
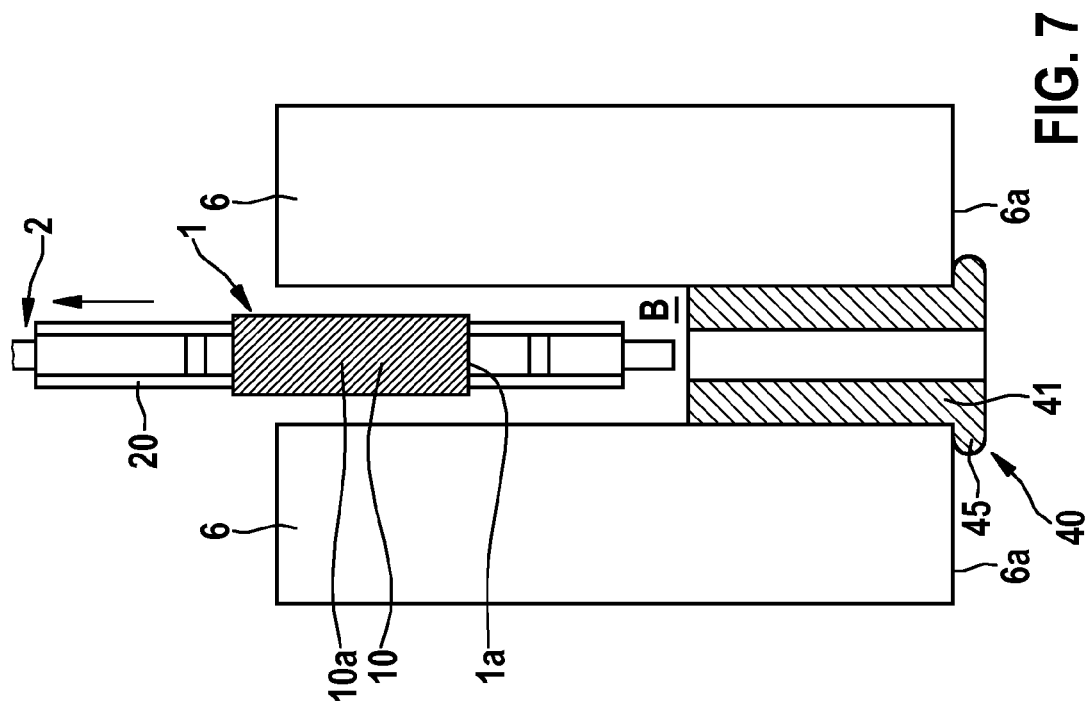

As is shown in FIGS. 3 through 8, the capsule 40, along with the stent 1 held in it, is inserted, in a vertically downward insertion direction E, into the area B between the opened pressure plates 6, so that the stent 1 can be supported, through the capsule 40, against the stop 7 positioned beneath the area B (see FIG. 3). The capsule 40 prevents the face 1a of the stent 1 from making direct contact with the stop 7 and the outer surface 10a of the wall structure 10 of the stent 1 from making direct contact with the pressure plates 6, so that the stent 1 is protected from contamination by contact with the pressure plates 6 or with the stop 7. The pressure plates 6 are then moved so that they hold the stent 1 with the capsule 40 between them, so that the stop 7 can be withdrawn, e.g., in the insertion direction E (see FIG. 4). The balloon catheter 2 with its balloon 20 is now inserted in the insertion direction E into the interior 11 of the stent 1 (see FIG. 5), and the stent 1 is pre-crimped on the balloon 20 by means of the pressure plates 6, which act, through the capsule 40, on the outer surface 10a of the wall structure 10 of the stent 1 (see FIG. 6). After this, the balloon catheter 2 with stent 1 crimped on it is withdrawn from the area B in the direction opposite the insertion direction E (see. FIG. 7), and the capsule 40 can be removed downward by corresponding opening of the pressure plates 6 (see FIG. 8).

The radial deformability of the capsule 40 allows the stent 1 to be pre-crimped on the catheter 2 when the capsule 40 is present. It is advantageous if (but not necessary that) the main component of the deformation of the capsule 40 be, according to one embodiment, reversible. This loosens the stent 1 from the capsule 40 after the pre-crimping (the stent 1 mainly undergoes plastic deformation due to the pre-crimping).

Enlarging the outside diameter at one lower end of a wall 41 of the capsule 40 extending in a peripheral direction U of the capsule 40 gives the capsule 40 projection 45, i.e., a bulge, which preferably extends in the peripheral direction U and which sticks out toward the outside in the radial direction R.

Figure 8:
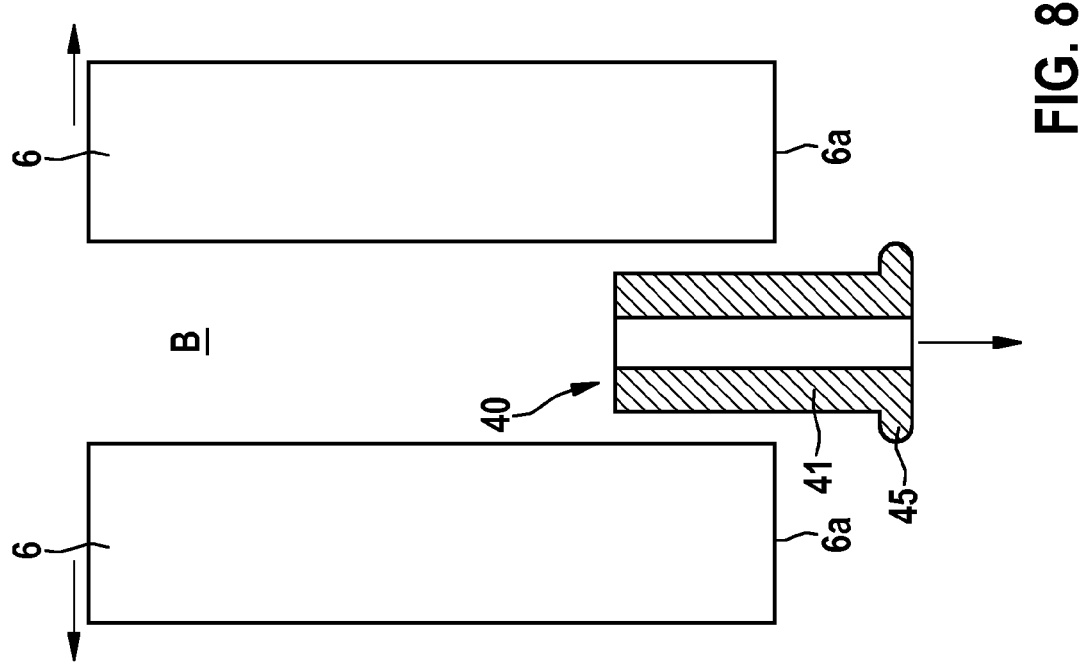

This allows the pressure plates 6 to be used to remove the capsule 40 from the stent 1 after the pre-crimping. As can be seen in FIGS. 7 and 8, after the actual pre-crimping, the pre-crimping head 6 is opened to a diameter that lies between the outside diameter of the capsule 40 and the outside diameter of the projection or the bulge 45. If the pre-crimped catheter 2 is now withdrawn from the pre-crimping head 6 or from the area B (see FIG. 7), the capsule 40 with the projection 45 catches on the bottoms 6a of the pressure plates 6.

The capsule 40 can be designed either as a disposable article or also as a reusable article that can be cleaned. Therefore, it is advantageous that the design be as simple as possible. Furthermore, according to one embodiment, the capsule 40 can also be provided with means of identification (a barcode or something similar) which serves, e.g., for unique traceability of the stent 1. This allows the system to assign the stent 1 in an unambiguous manner.

Possible materials for the capsule 40 are, for example, an HDPE and especially also PA12 or PTFE. One embodiment provides that the wall 41 of the capsule 40 have a gap 42 (see FIGS. 1 and 2) whose width preferably corresponds to the reduction in the circumference of the stent 1 or of the wall structure 10 caused by the pre-crimping.

The projection or the bulge 45 can be produced, e.g., by thermal deformation of a tubular blank of the capsule 40 or of the wall 41. The inside diameter of the tube or the wall 41 is preferably less than the original outside diameter of the (not yet pre-crimped) stent 1. This holds the stent 1 in the capsule 40 or in the wall 41 by a non-positive connection.

The inside diameter of the tube or the wall 41 is preferably greater than the outside diameter of the processed, i.e., pre-crimped stent 1. This makes it easier for the capsule 40 to be loosened from the stent 1 after pre-crimping.

Another sample embodiment provides that the capsule 40 have a wall 41 that has a gap 42 extending in the axial direction, this wall 41 having an inside diameter is the same as the outside diameter of the processed stent 1. This holds the stent 1 by a non-positive connection, and the capsule 40 is no longer loosened from the stent 1 after pre-crimping.

Figure 10:
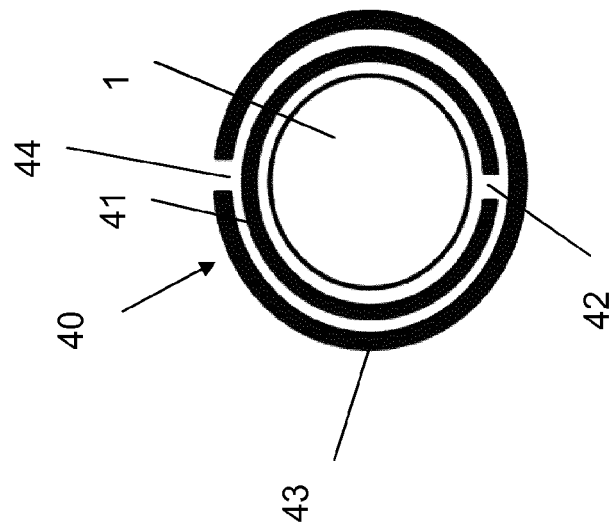
FIG. 10 a schematic sectional view of another embodiment of the capsule.
Figure 9:
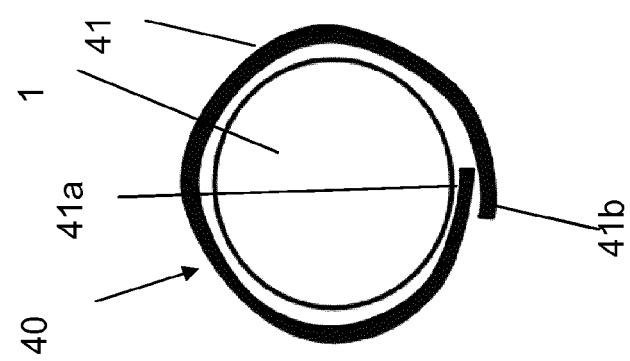
FIG. 9 a schematic sectional view of another embodiment of the capsule.

Another sample embodiment provides that the capsule 40 can have a wall 41 with overlapping edges 41a, 41b, as is shown in FIG. 9. Furthermore, the capsule 40 can have two walls 41, 43, each with a gap 42, 44, the gap 42, 44 of the respective wall 41, 43 being covered by the other wall 43, 41 (see FIG. 10).

In principle, it is not absolutely necessary for the capsule 40 or the wall 41 to have a slit or a gap 41. If the reduction in diameter of the stent 1 caused by pre-crimping is relatively small, the elastic deformability of a tubular capsule 40 without a slit is also sufficient.

Figure 11:
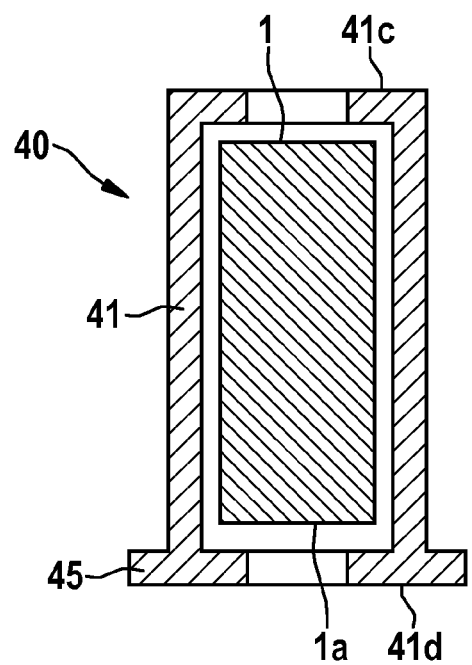
FIG. 11 a schematic sectional view of another embodiment of the capsule.

Furthermore, the stent 1 can also be held in the capsule 40 in a form-fit manner by capsule areas 41d, 41c, as shown in FIG. 11.

Using the capsule 40 as a protection device can provide an economical solution for preventing cross contamination during machine transportation and pre-crimping of a drug-coated stent 1.

FIGS. 12 through 28 show aspects of the inventive process or embodiments that are alternatives to the capsule 40, which is replaced by a support 50 that forms at least the first part 4 of the protection device.

Figure 13:
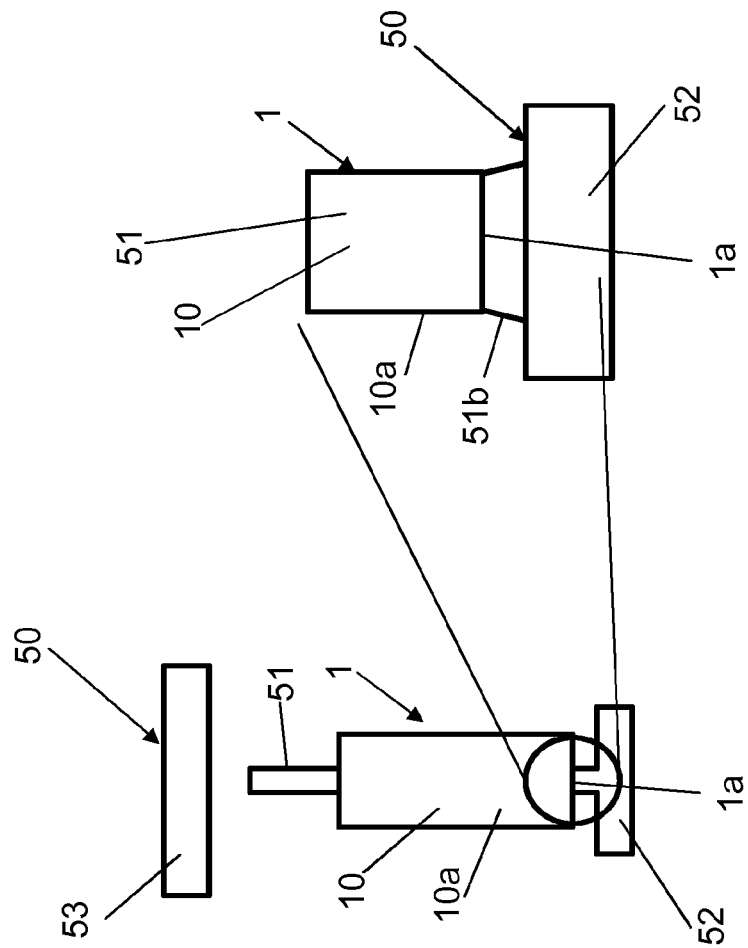
FIG. 13 a detachable head part of the support according to FIG. 12 and flaring (a cone shape) of a pin of the support.
Figure 12:
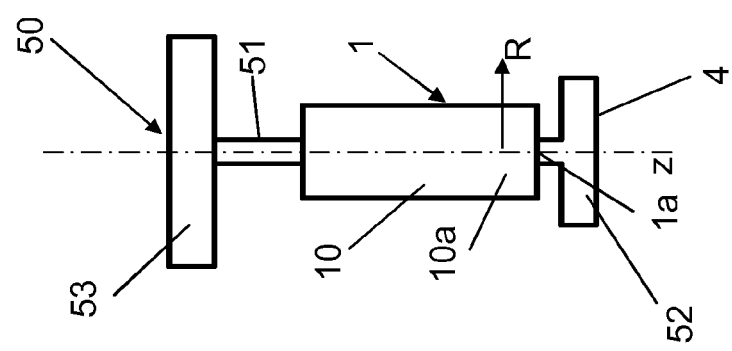
FIG. 12 a schematic side view of another embodiment of a protection device in the form of a support for the stent.
Figure 15:
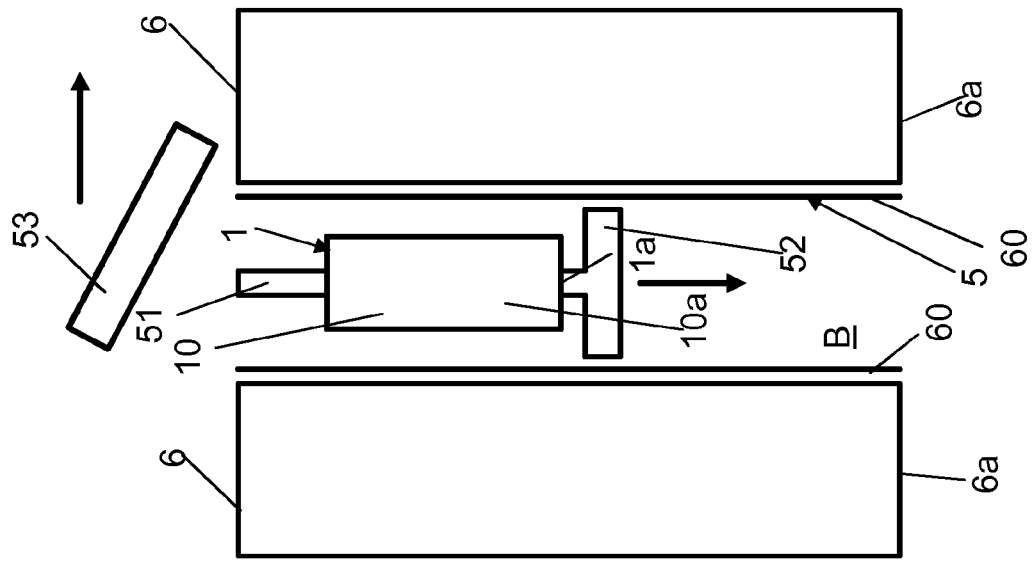
FIG. 14-19 an embodiment of the process for arranging or crimping the stent on a balloon of a balloon catheter using the protection device according to FIGS. 12 and 13.
Figure 14:
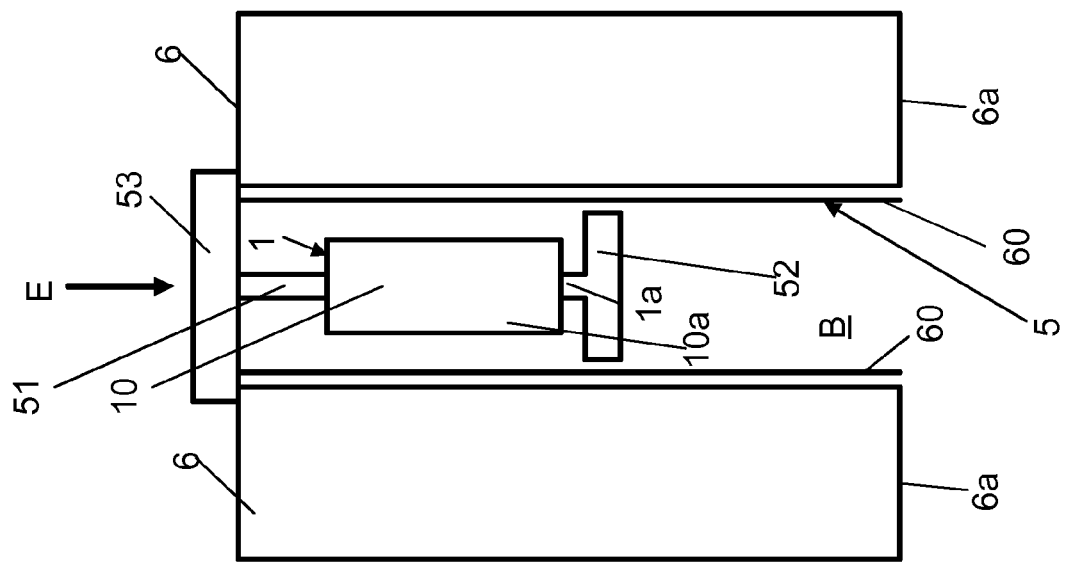

The support 50 serves to support the stent 1 and can be, e.g., dumbbell-shaped to protect the stent 1, and according to one embodiment that is shown in FIGS. 12 and 13 the support 50 has, e.g., a pin 51, that is inserted into the interior 11 of the stent 1 before the stent 1 is arranged in the aforementioned area B between the pressure plates 6 (see FIG. 14).

Figure 16:
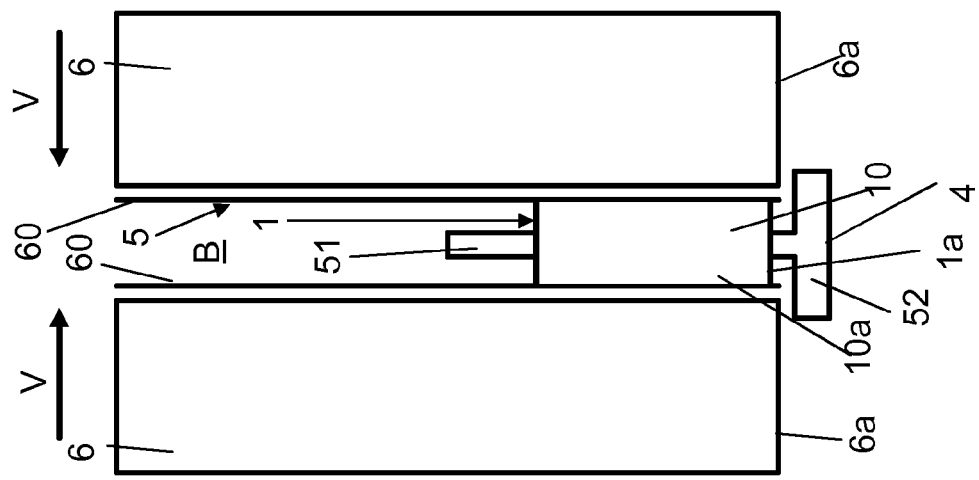
Figure 17:
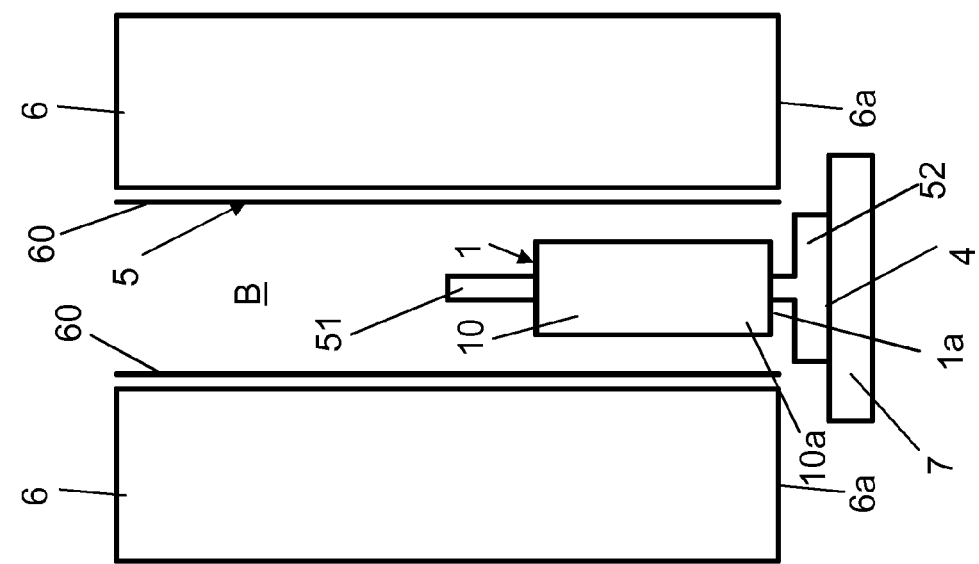
Figure 18:
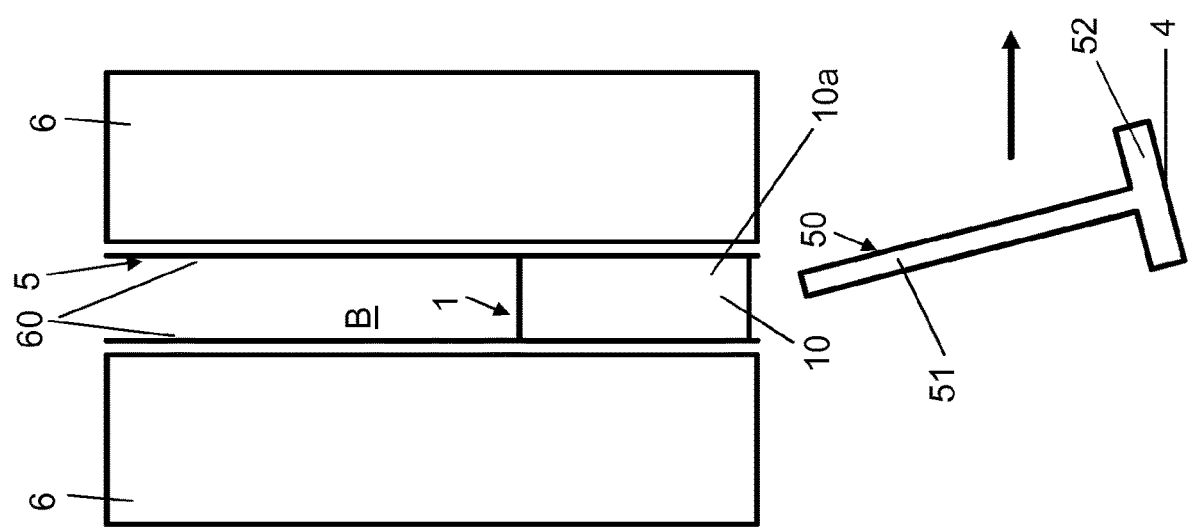

The support 50 along with stent 1 is preferably inserted into the aforementioned area B between the pressure plates 6 so that the support 50 makes contact with the stop 7 or the stent 1 is supported against the stop 7 through the support 50, so that a direct contact between the stent 1 and the stop 7 is avoided with respect to the stop 7 (see FIG. 16).

The support 50 preferably has a base 52 connected with the pin 51, this base 52 projecting in the radial direction R to protect the stent 1 over its outer surface 10a. In the same way, the support can have a head part 53 that is, e.g., detachably connected or connectable with the pin 51, this head part 53 also projecting in the radial direction R beyond the outer surface 10a of the stent 1 (see FIG. 12).

The two ends 52, 53 (i.e., e.g., the base 52 and the head part 53) of the dumbbell 50 or of the support 50 form the supporting surface of the support 50 in the transport system, or offer gripping surfaces for a gripper. Therefore, the ends 52, 53 have a larger outside diameter than the stent 1 itself.

The support 50 is preferably designed so that one side, e.g., the head part 53, can be opened both manually and by machine (e.g., by means of a thread, a magnet, or by means of a snap connection). This makes it possible for the stent 1 to be assembled in a manual preparatory step. Ideally, this is done immediately after the actual stent production (coating). This allows the support 50 simultaneously also to function as a transport container between the production locations. Furthermore, the stent 1 can then be loosened from the support 50 during the corresponding process step in the system, e.g., during pre-crimping (see FIG. 18).

The dumbbell design allows, in particular, the stent 1 to be grasped in the pre-crimping head or if it is arranged in the area B, even if is it still being guided by parts of the support 50. In addition, it allows processing of the stent 1 in other process steps, e.g., during coating or during a visual inspection.

Furthermore, the support 50 can also be provided with means of identification (e.g., a QR code, RFID, or something similar) which serves, e.g., for unique traceability of the stent 1. This allows the system to assign the stent 1 in an unambiguous manner.

The support 50 can be designed either as a disposable article or also as a reusable article that can be cleaned.

As can be seen in detail in FIGS. 15 through 19, a stent 1 of a batch is assembled on the support 50, e.g., immediately after coating and hardening, the pin 51 being inserted into the interior 11 of the stent 1, so that the stent 1 rests, e.g., on the base 52 or on a cone-shaped end section 51*b* of the pin 51 (see FIGS. 12 and 13). Furthermore, it is conceivable for the stent to be fixed on the pin 51 by means of a torsion spring 56 (see FIG. 26).

To save space, the balloon catheters 2, some of which are relatively long, are preferably processed in the vertical direction, i.e., the catheters 2 are moved vertically into the processing level (e.g., crimping head or area B) at the respective processing stations. Thus, the actual processing level lies beneath the transport level.

The stent assembly begins, in particular, with a pre-crimping step. This involves roughly positioning the stent 1 on the balloon 20 and crimping the stent 1 until it lies tightly against the balloon 20, but is still movable. When this is done, the pressure plates 6 are covered with one or more film sheets 60 made, in particular, of PTFE, to avoid cross contamination. That is, here the film sheet(s) 60 form the second part 5 of the protection device.

To pre-crimp the stent 1, it can, together with its support 50, be inserted, e.g., through a slide, vertically downward in an insertion direction E into the area B between the pressure plates 6, so that, e.g., the head part 53 of the support 50 comes to lie on the pressure plates 6 (see FIG. 14). Then, the upper head part 53 of the support 50 is loosened, e.g., by machine, from the lower part or from the pin 51, and the head part 53 is removed.

The lower part of the support 50, here, e.g., the pin 51 and the base 53, now falls, together with the stent 1, onto the lower end of the area B, where a mechanical stop 7 defines the position of the support 50 (and thus of the stent 1) (see FIG. 16). The mechanical stop 7 is preferably arranged lower down, by at least the thickness of the base, than the respective lower end of the pressure plates 6. Now, if the pressure plates 6 close (see FIG. 17), the stent 1 is held and the lower part of the support 50, i.e., the pin 51 and the base 52, can be removed together (see FIG. 18).

Figure 19:
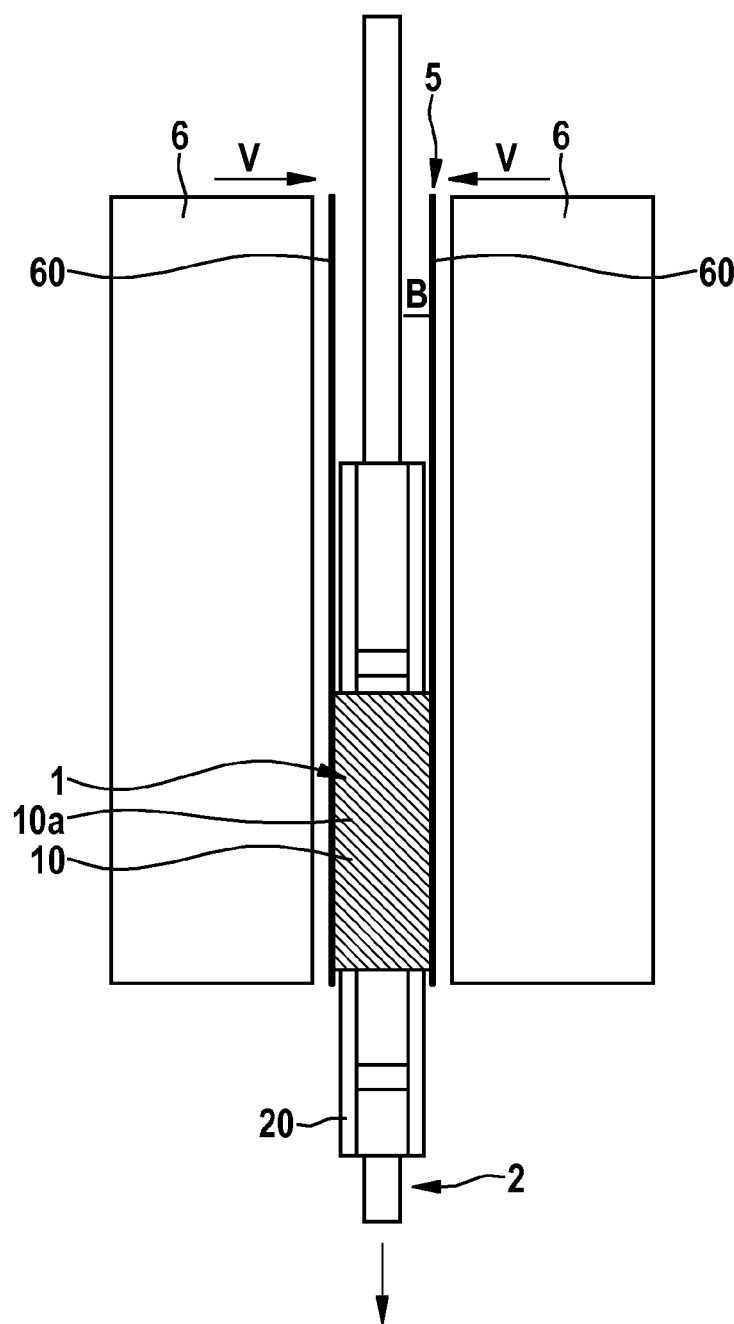
Figure 21:
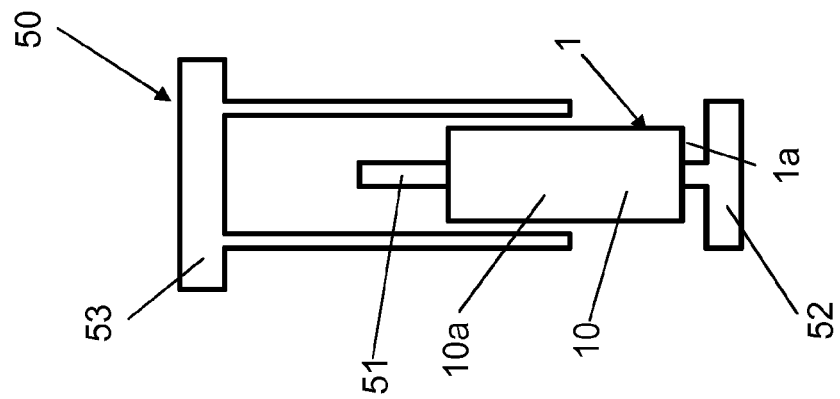
FIG. 20-21 a variation of the head part of the support of FIGS. 12 and 13.
Figure 20:
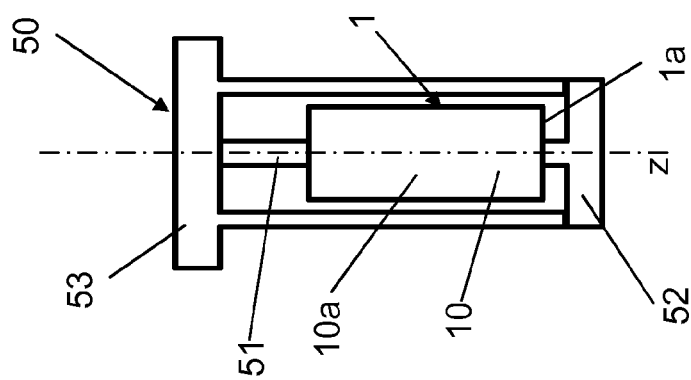
Figure 23:
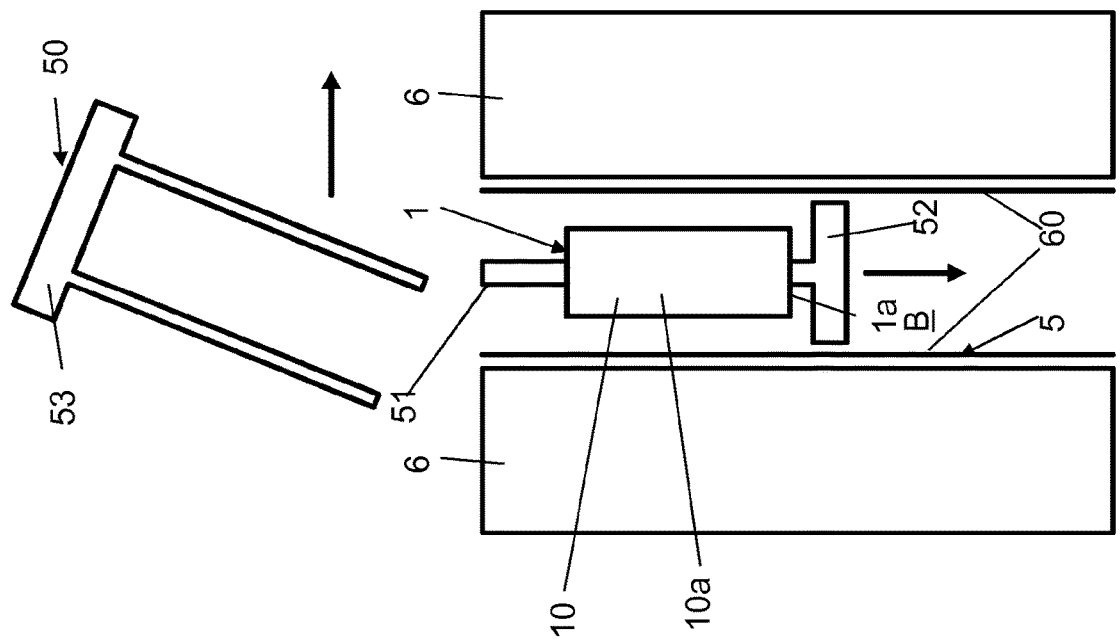
FIG. 22-23 an embodiment of the process for arranging or crimping the stent using the support according to FIG. 20 or 21.
Figure 22:
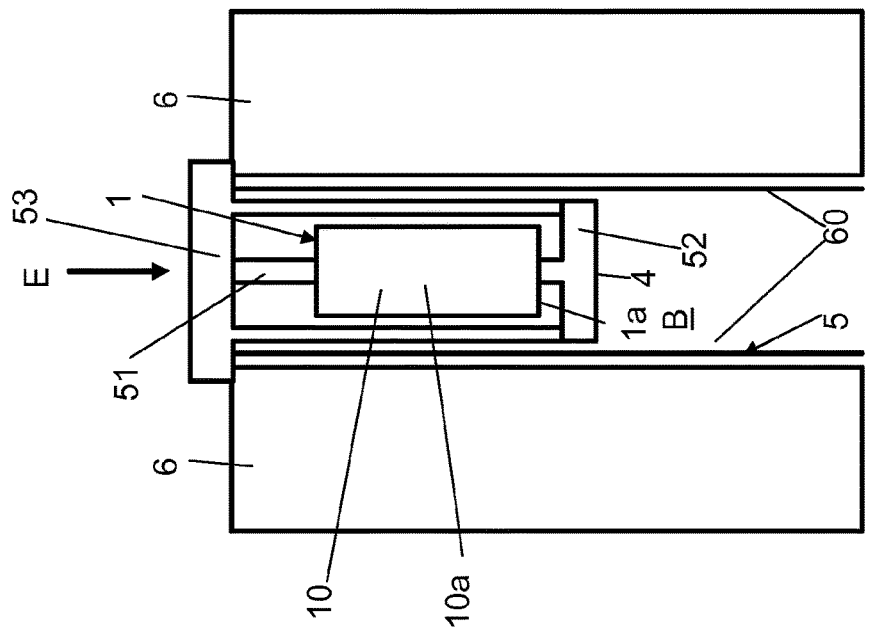
Figure 27:
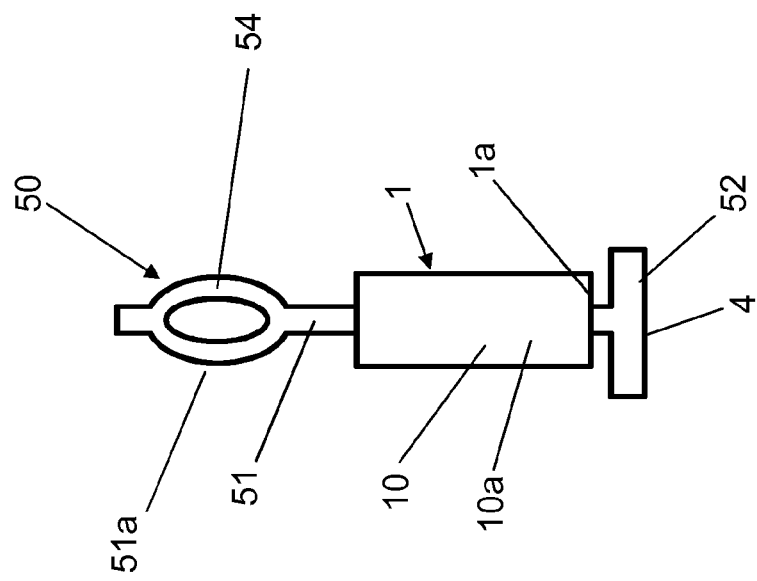
FIG. 27 another embodiment of the support.
Figure 28:
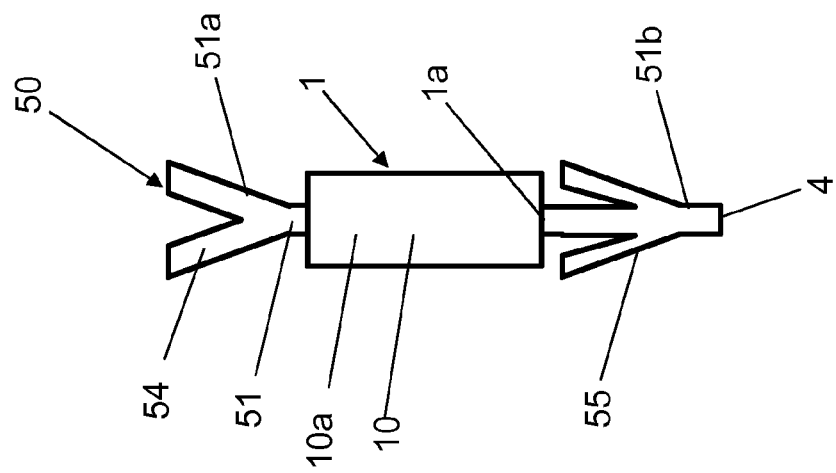
FIG. 28 another embodiment of the support.
Figure 29A:
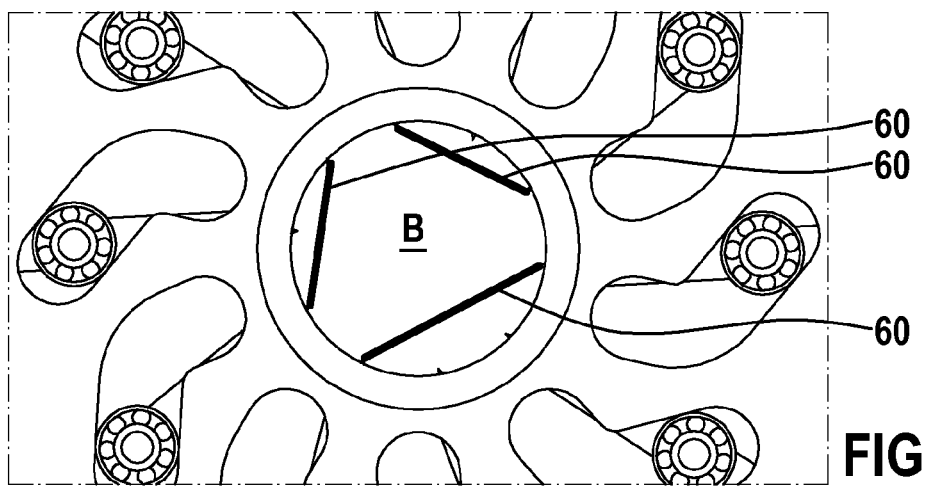
FIG. 29 (A)-(F) another embodiment of the process for arranging or crimping the stent using a film tunnel to protect the stent.
Figure 29B:
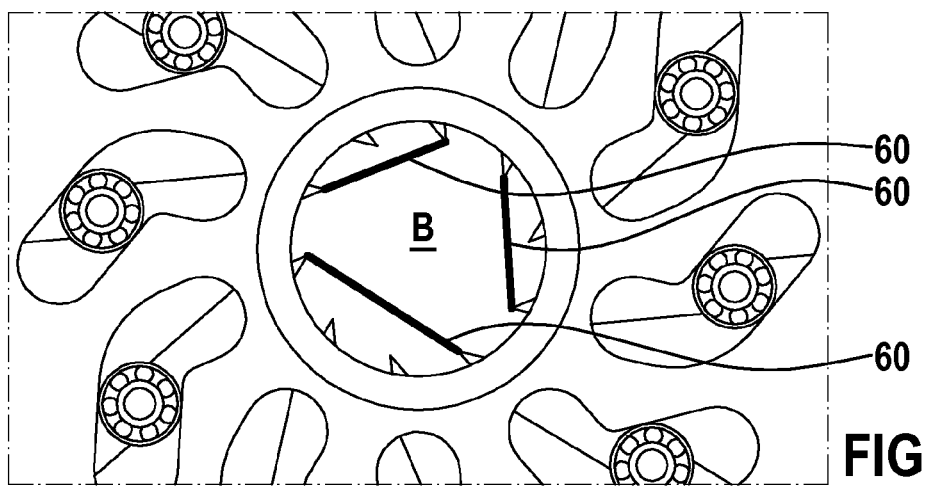
Figure 29C:
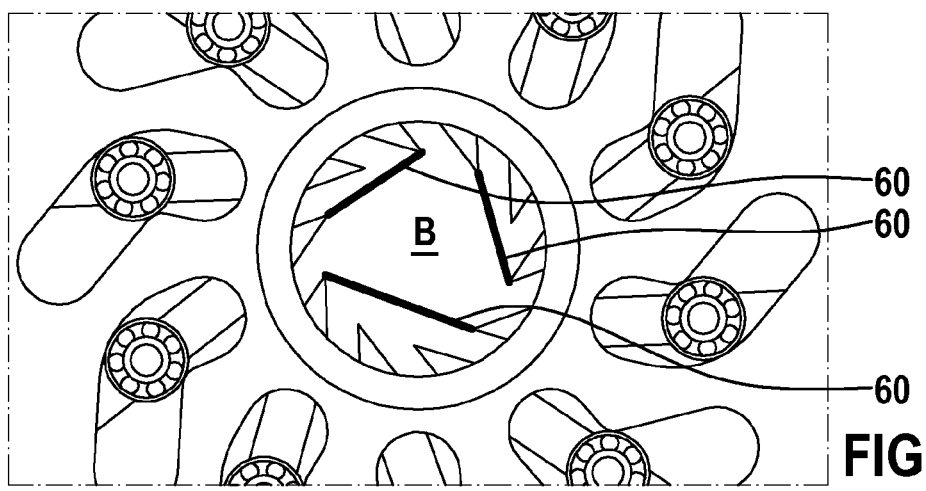
Figure 29D:
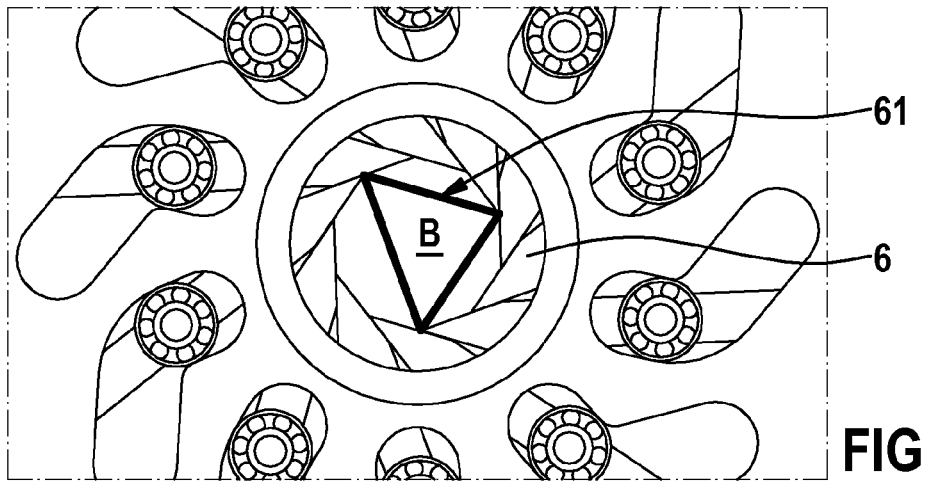
Figure 29E:
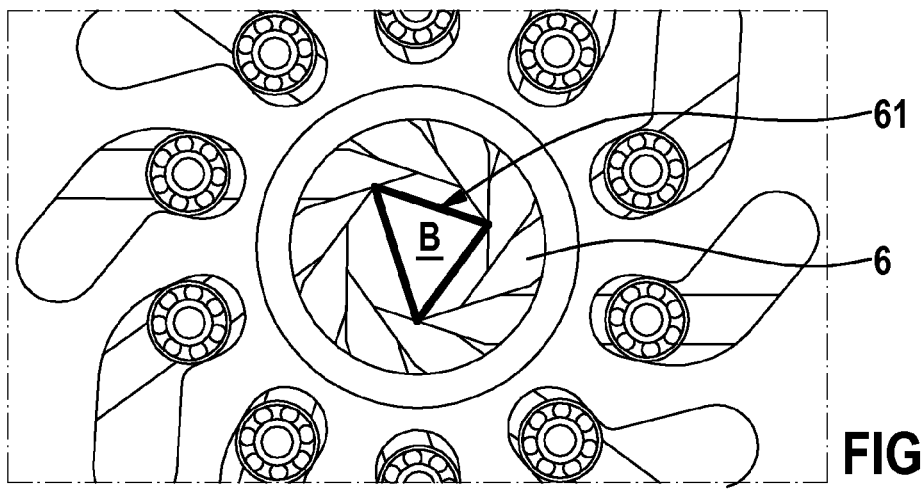
Figure 29F:
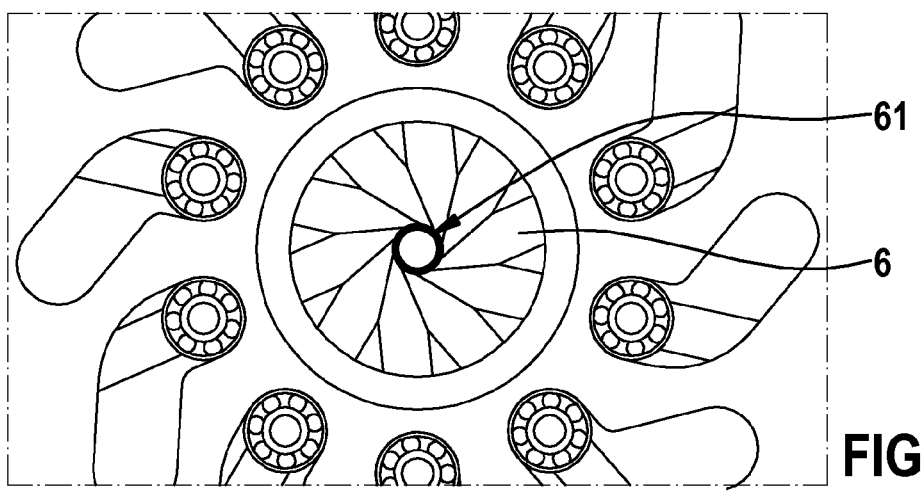
Figure 30A:
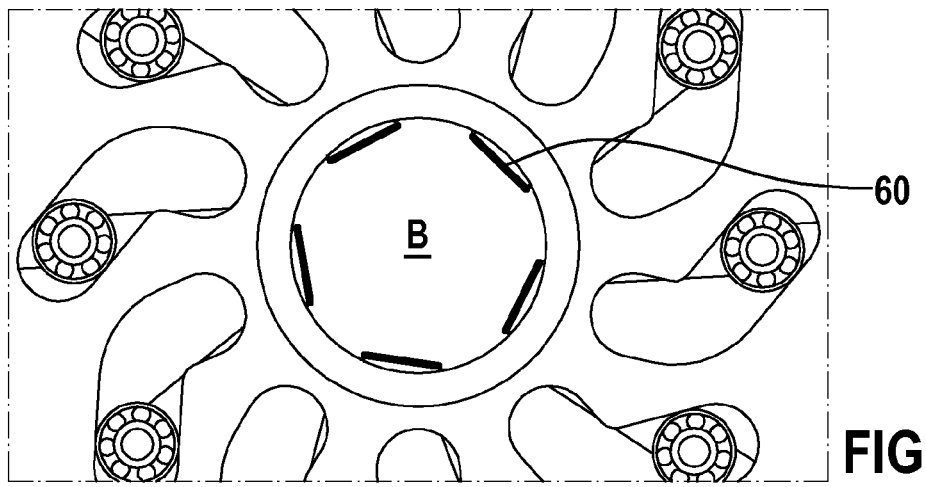
FIG. 30 (A)-(F) another embodiment of the process for arranging or crimping the stent using a film tunnel to protect the stent.
Figure 30B:
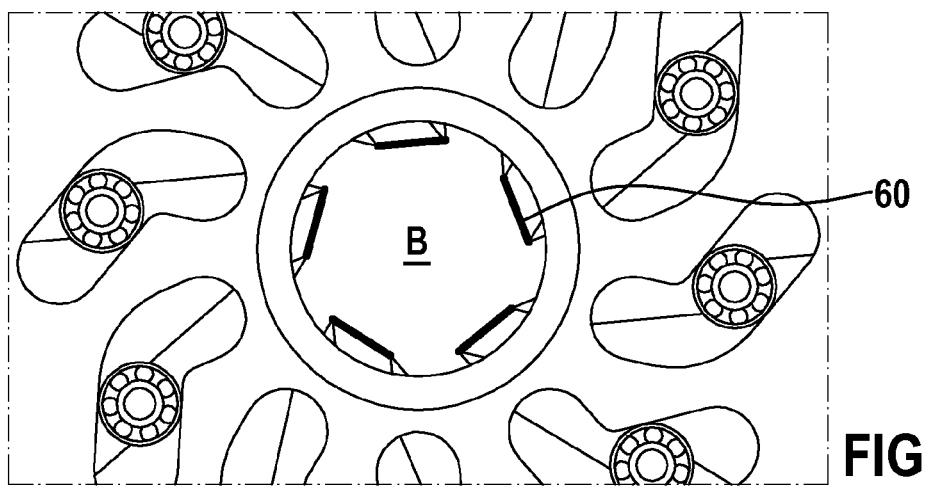
Figure 30C:
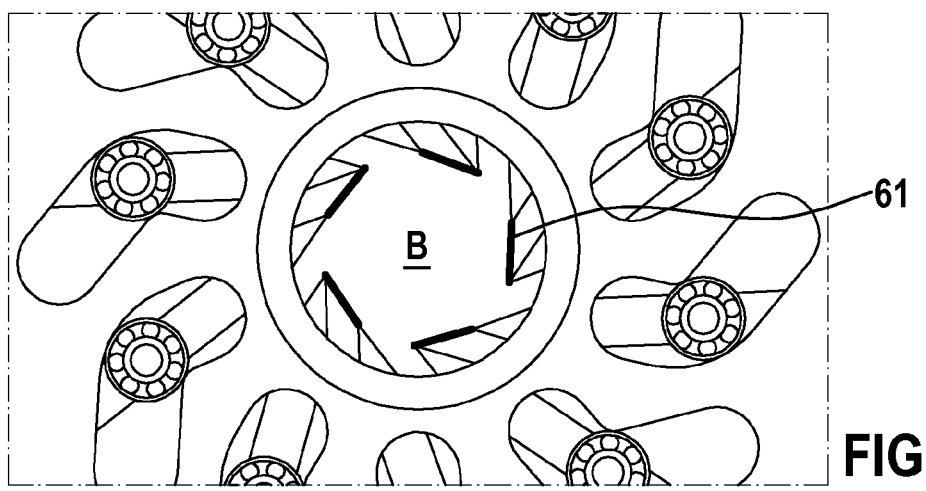
Figure 30D:
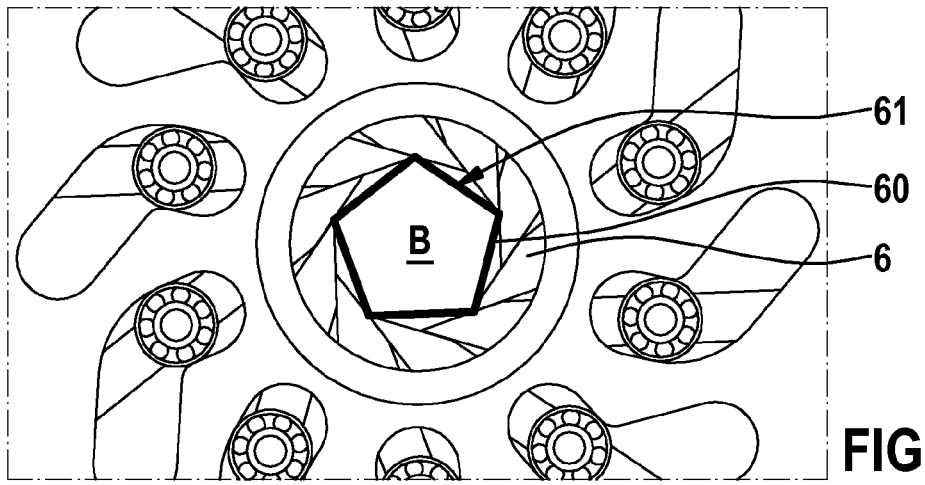
Figure 30E:
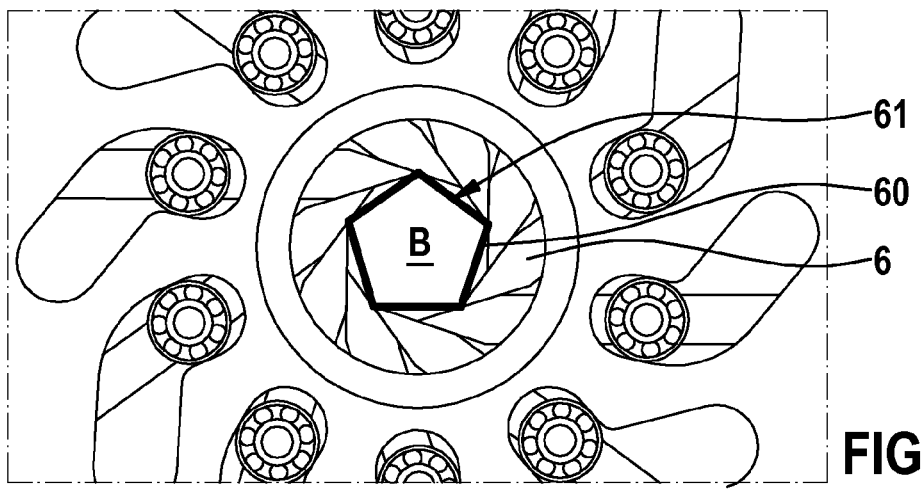
Figure 30F:
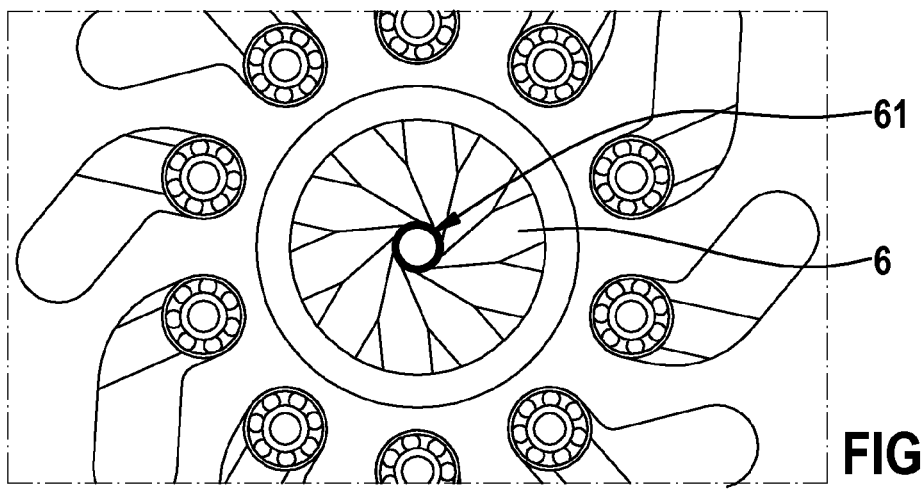

The balloon catheter 2 is now pushed through the area B into the interior 11 of the stent 1, as is shown in FIG. 19, so that the wall structure 10 of the stent 1 surrounds the balloon 20. The pressure plates 6 now crimp or pre-crimp the stent 1 onto the balloon 20 (FIG. 19). The components 51, 52, 53 of the support 50 can, in particular, be collected, cleaned, and then reused as a unit.

FIGS. 24 and 25 show how it might be possible to do without a separate head part 53, to simplify the process further. To accomplish this, the pin 51 can, e.g., project out of the interior 11 of the stent 1 far enough that the stent 1 cannot make contact with a plane surface F or a surface of the transport system (e.g., a slide), if the base 52 and an end 51*b* of the pin 51 lie on the surface F.

Furthermore, the head part 53 according to FIGS. 20 through 23 can also be designed so that it is detachably connectable with the pin 51 and/or the base 52 and forms a protective sheath surrounding the outer surface 10*a* of the stent 1 when the head part 53 is connected with the pin 51 and/or with the base 52 in the way it is supposed to be. Here again, the head part 53 is removed after the support 50 along with stent 1 has been arranged in the area B between the pressure plates 6 (see FIG. 23).

Furthermore, the support 50 can have, instead of a removable head part 53 at an end section 51*a* of the pin 51, a spring element 54 that allows the stent 1 to be threaded onto the pin 51. In the same way, the plate-shaped base 52 can be replaced by another second spring element 55, which can be provided instead of the aforementioned base 52 at the opposite end section 51*b* of the pin. Here, the support 50 then rests on the stop 7 through the second spring element 55 or an end of the pin 51 of the support 50.

Finally, FIGS. 29 through 40 show other embodiments of the inventive process, wherein the first part 4 of the protection device here is preferably formed by a film sheet 62 that is arranged on the stop 7, so that the stent 1 cannot receive any direct contact with the stop 7. The second part 5 of the protection device is formed by a flexible film sheet 60, which is preferably guided by means of a guide device, in particular by means of guide rollers 71 (see, e.g., FIGS. 31 and 32), or by multiple separate flexible film sheets 60, each of which can be individually guided.

Once again, the actual assembly of the stent begins with the pre-crimping step. This involves roughly positioning the stent 1 on the balloon 20 by means of the pressure plates 6 of the crimping tool and crimping the stent 1 until it lies tightly against the balloon 1, but is still movable. The position of the stent 1 within the pre-crimping head or the area B between the pressure plates is preferably defined in the insertion direction E. This is done, e.g., by means of a withdrawable mechanical stop 7, which is shown, e.g., in FIG. 35.

It is advantageous if all components potentially in contact with the stent 1 during pre-crimping of the stent 1 on the balloon 20 of the balloon catheter 2 are covered with film sheets 60, 62 that can be retracted or rolled up. This ensures that a drug put on the stent always comes in contact with a fresh part of the respective film or film sheet.

To allow the stent 1 or balloon catheter 2 to be guided in the area B between the pressure plates 6, it is preferable that at least three film sections be provided, these at least three film sections being opposite one another. These film sections can be provided by a single guided film sheet 60 or by three or more than three separate film sheets 60.

As is shown, e.g., in FIGS. 29 (A) through (F), film sheets 60, e.g., three film sheets 60, can be pulled through between adjacent pressure plates 6 and arranged in the area B. As the pressure plates 6 are moved in the direction toward the outer surface of the stent 1 and the balloon 20 arranged in it (for clarity, FIG. 29 does not show stent 1 and balloon 20), the three film sheets 60 are moved toward one another by the movement of the pressure plates 6, until together they produce a film tunnel 61, that surrounds the stent 1 in the peripheral direction. Now, the outer surface 10*a* of the stent 1 can no longer come in direct contact with the pressure plates 6.

As an alternative to three film sheets 60, it is also possible to use five film sheets 60, as is illustrated in FIGS. 30 (A) through (F). Instead of separately guided and driven film sheets 60, it is also possible to produce a corresponding number of film sections 63 in the area B by guiding, e.g., by guide rollers 71, a single film sheet 60 through between the respective adjacent pressure plates 6 into the area B between the pressure plates 6, so that as the pressure plates 6 are moved in the direction toward the outer surface 10*a* of the stent 1, the aforementioned film tunnel 61 is formed, in which every two adjacent film sections 63 contact one another.

Figure 31:
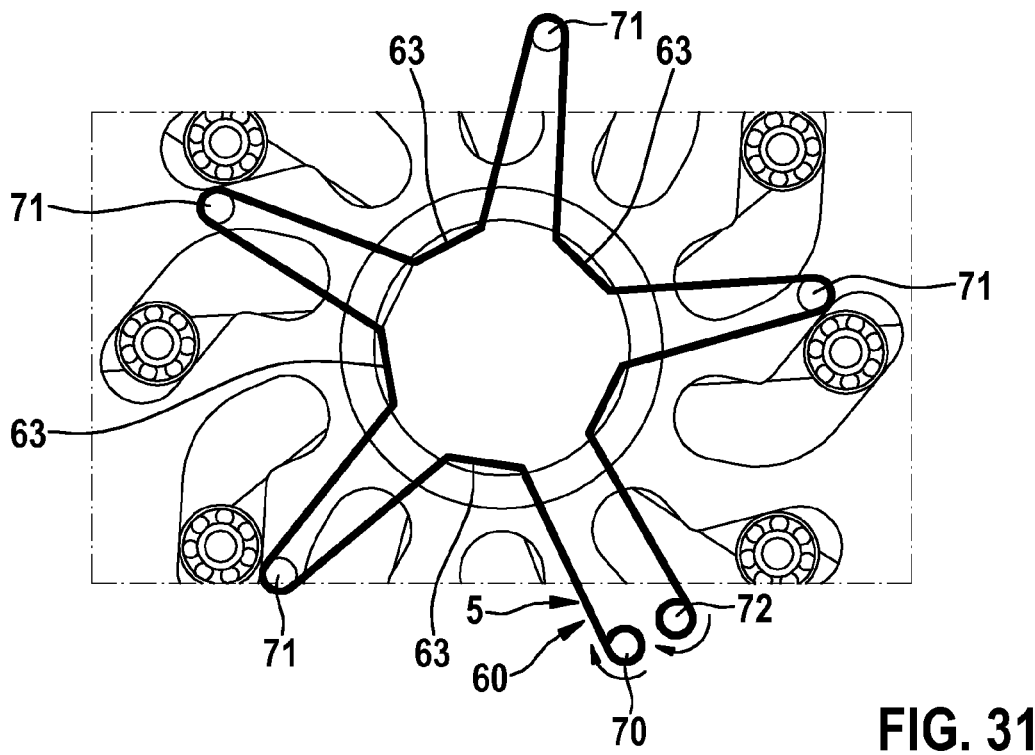
FIG. 31-32 another embodiment of the process for arranging or crimping the stent using a film tunnel to protect the stent.
Figure 32:
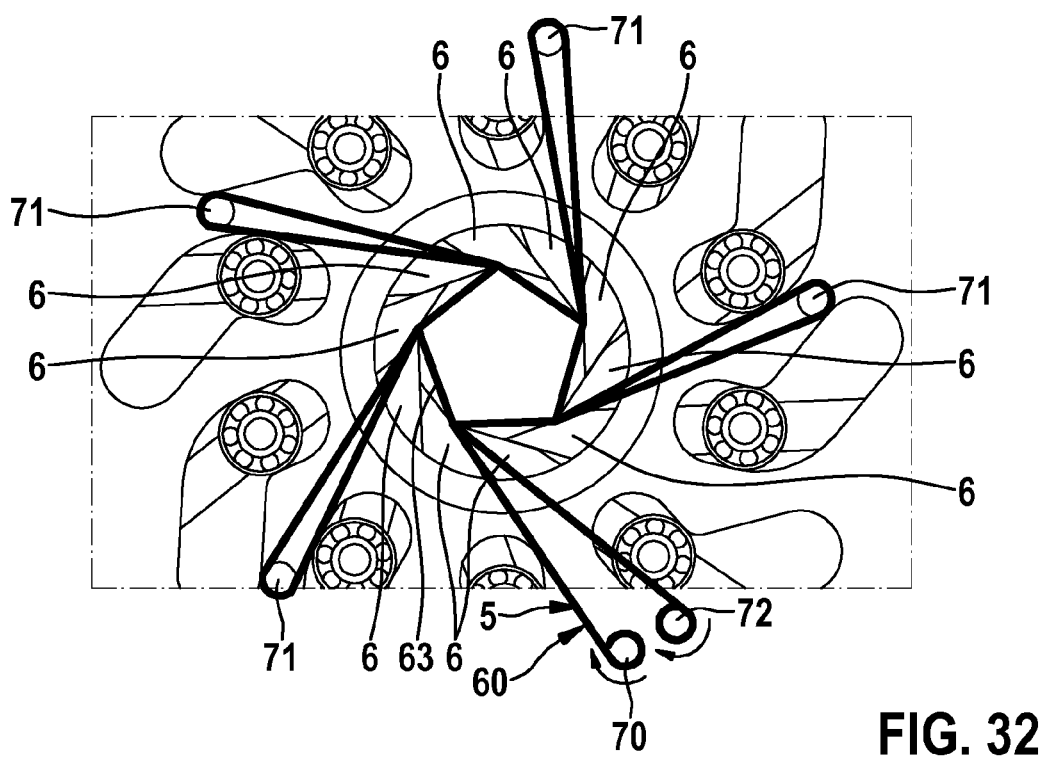

Relating to this, FIGS. 31 and 32 show an embodiment in which a film sheet 60 is guided by guide rollers 71 so that five film sections 63 are formed in the area B between the pressure plates 6 (here, e.g., 10 pressure plates 6), which then form the aforementioned film tunnel 61 as the pressure plates 6 travel in the direction toward the stent 1. This can involve the film sheet 60 being unwound from a feed roller 70 and onto a take-up roller 72, which can be driven by means of a motor to accomplish this. Alternatively, of course it is also possible to provide separate film sheets 60, each of which can be separately guided and driven. Every individual film sheet 60 can be unwound, e.g., from a feed roller and wound up onto a take-up roller, which is, e.g., driven.

The mechanical stop 7 is preferably protected with a separate film sheet 62, as is shown, e.g., in FIGS. 33 through 37.

After the pre-crimping, the stent 1 is possibly repositioned and undergoes final crimping. As a rule, repositioning is necessary, since the pre-crimping and the radial tapering still allow the position of the stent 1 to be slightly changed. Thus, repositioning allows, e.g., a more exact positioning between X-ray markers of the balloon catheter and thus makes it easier for the doctor to position the stent using the X-ray picture in the case of a stenosis.

Vertical processing of the balloon catheter 2 is advantageous, especially to save space.

To arrange the stent 1 on the balloon 20 of the balloon catheter 2, the stent 1 is transported to the pressure plates 6, e.g., through a magazine, by a slide system, grippers, or something similar.

Figure 35:
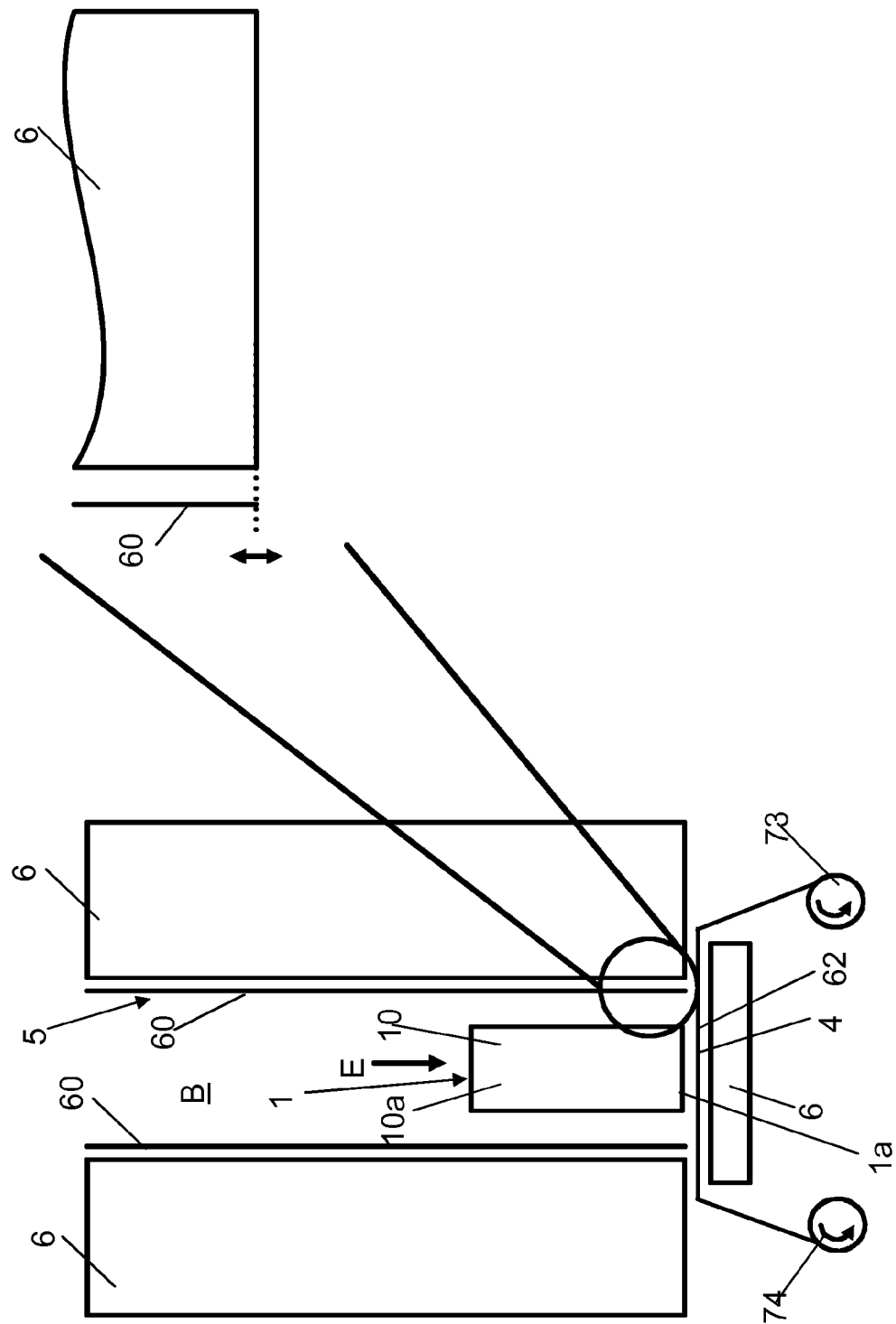
FIG. 35-40 a variation of the process wherein sections of the stent project out of an area surrounded by the pressure plates.
Figure 36:
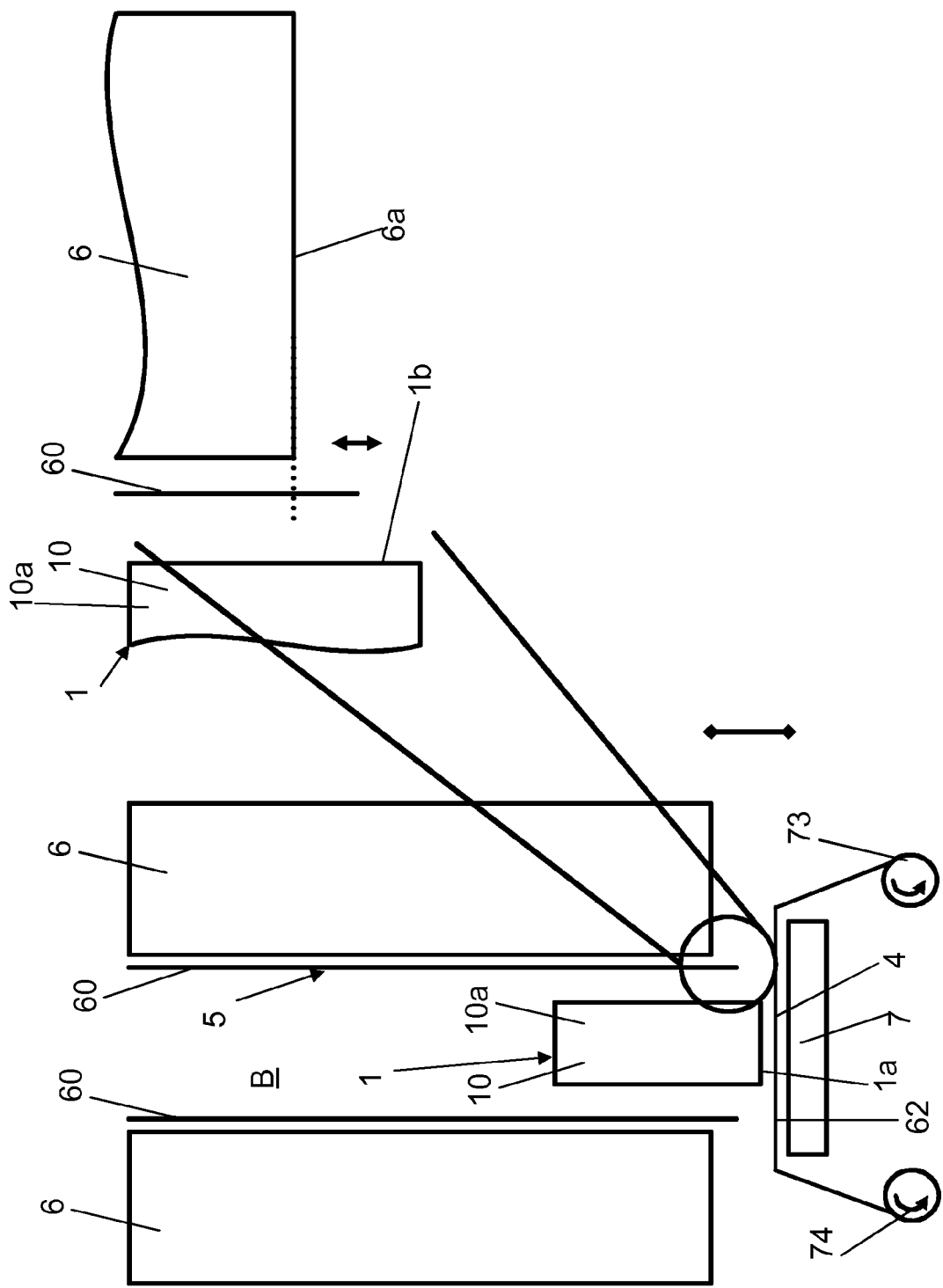

As is shown in FIGS. 35 through 40, the stent 1 is then inserted in an insertion direction E into the area B between the pressure plates 6, e.g., by taking advantage of gravity, the stent 1 falling on the stop 7. This is shown, e.g., in FIG. 35. FIG. 36 shows an alternative arrangement of the stop 7, which is explained below.

Figure 38:
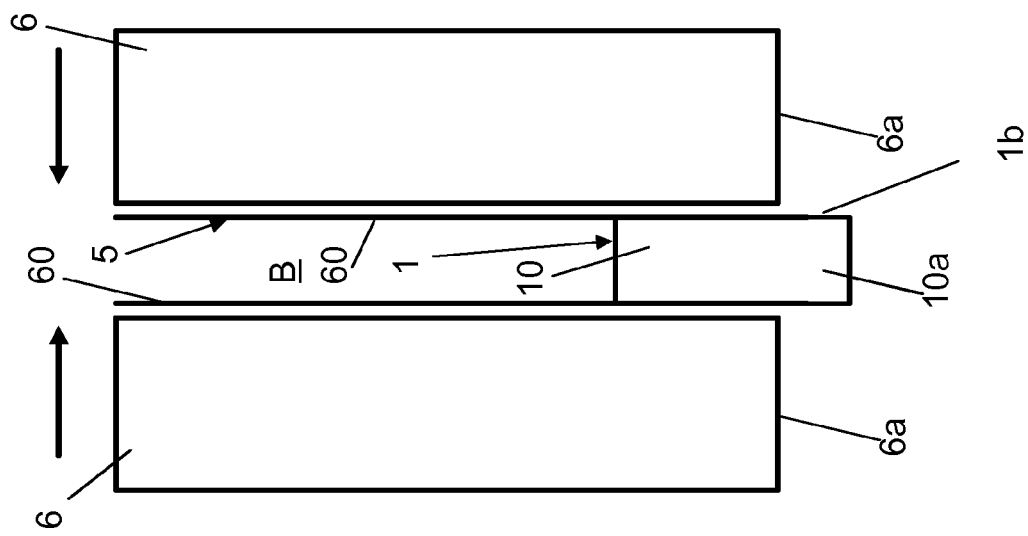
Figure 37:
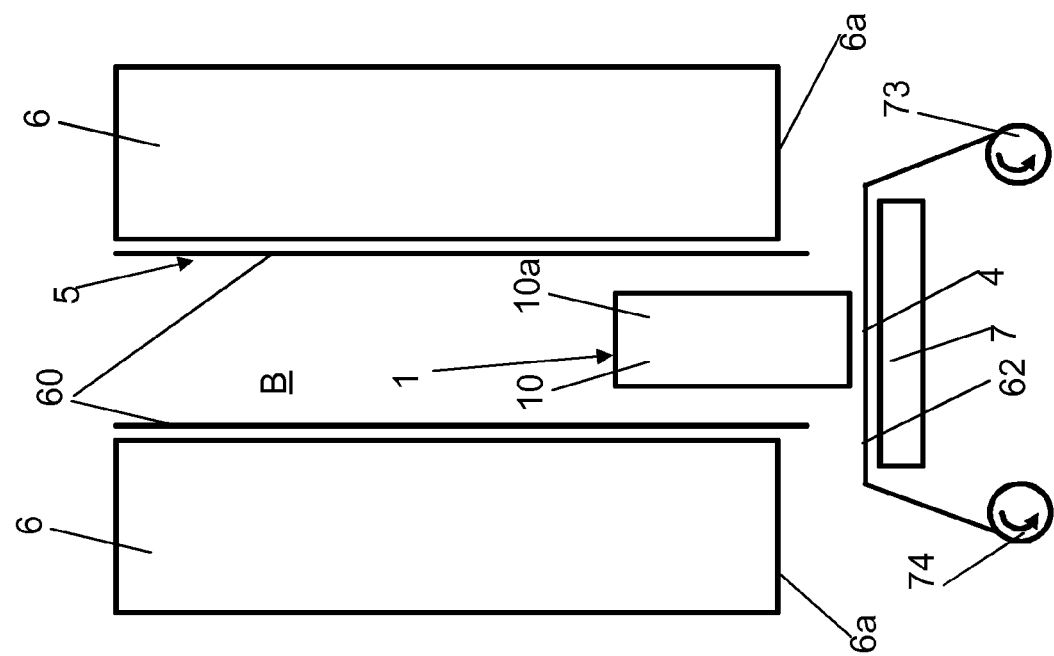
Figure 39:
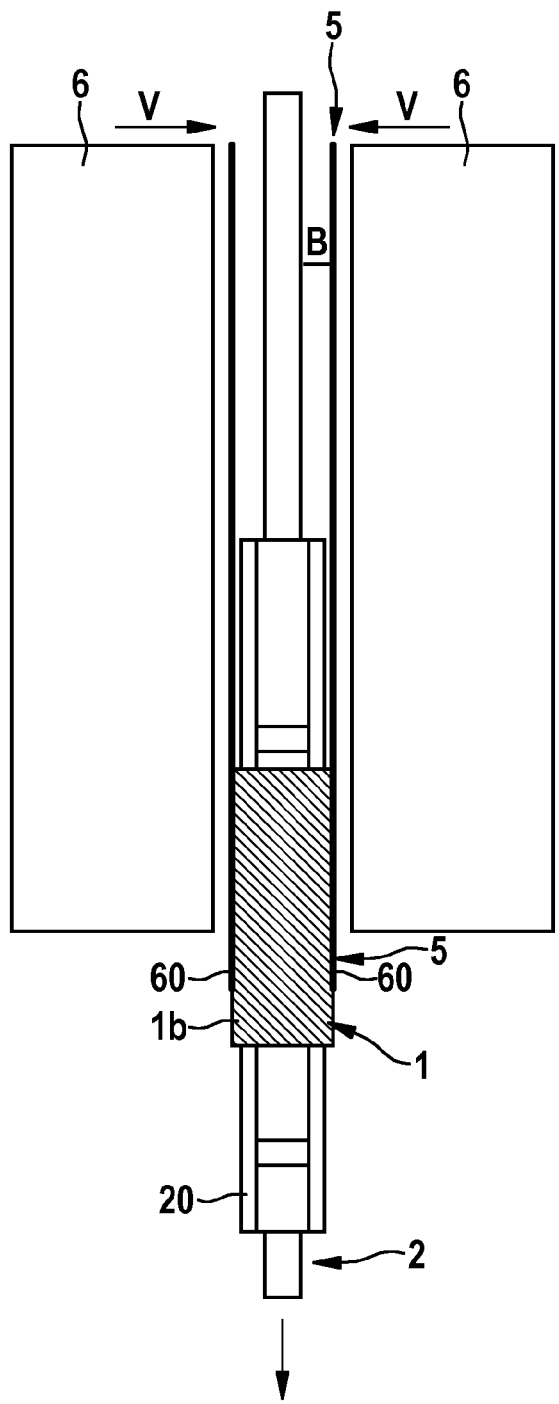

After the stent 1 is arranged on the stop 7 (with film sheet 62 between them), the pressure plates 6 are moved in the direction toward the outer surface 10*a* of the wall structure 10 of the stent 1, until the stent 1 is held by the pressure plates 6 (see FIG. 38). The stop 7 now moves back (e.g., in the insertion direction E) and the balloon catheter 2 can be pushed through the interior 11 of the stent from above, so that the balloon 20 is arranged in the interior 11 of the stent 1. Moving the pressure plates 6 in the direction toward the outer surface 10*a* of the stent 1 now pre-crimps the stent 1 onto the balloon 20 of the balloon catheter 2 (see FIG. 39).

Since the stent 1 is arranged in the aforementioned film tunnel 61 in the area B, the pressure plates 6 cannot make direct contact with the stent 1, but rather press against the stent 1 through the film sheets 60 or the film sections 63 of the film sheet 60. As was already explained above, this film tunnel 61 is realized by arranging, e.g., three or five film sheets 60 or three or five film sections 63 opposite one another in the area B, each of the at least one film sheets 60 being guided through between adjacent pressure plates 6, so that the film tunnel 61 is formed if the pressure plates 6 approach one another (see FIGS. 29 through 32). Depending on the embodiment of the pressure plates 6, the film sheets 60 or sections 63 can make contact from the start, or only after a certain reduction in the inside diameter of the area B.

The mechanical stop 7 beneath the pressure plates 6 can be protected with a film sheet 62 in a relatively simple manner. As is shown in FIG. 35, the stop 7 can be arranged flush with the bottoms 6*a* of the pressure plates 6. However, it is constructively difficult to ensure a corresponding exact coverage of the pressure plates 6 with the at least one film sheet 60 or film sections 63. Therefore, it turns out to be advantageous if the stop 7 is arranged so that it is not flush with the bottoms 6*a* of the pressure plates 6, as is shown in FIG. 36. This makes it possible to let the respective film sheet 60 or the respective film section 63 project beyond the bottom 6*a* of the respective pressure plate 6, as is shown in FIG. 36. Sections of the stent 1 also protrude downward out of the area B. That is, the stent 1 need not be completely enclosed by the side film sheets 60 or film sections 63. Thus, the film positioning needs to be less exact, and thus it is more robust.

Figure 40:
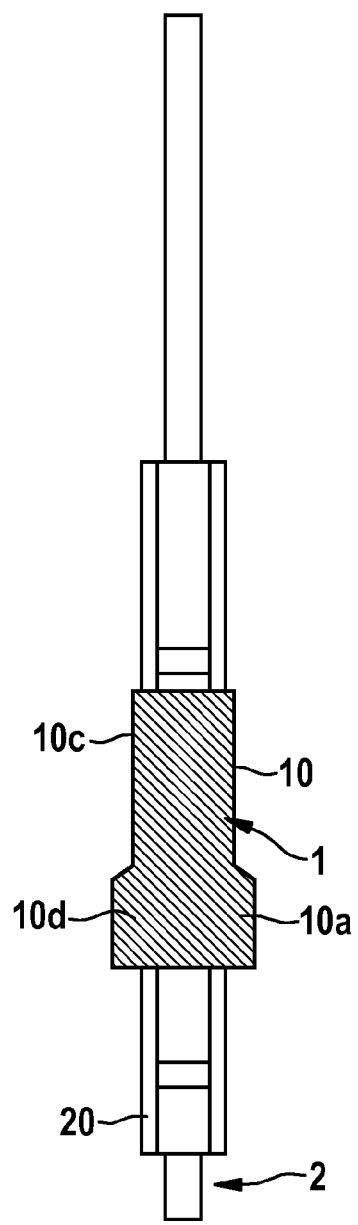

The pre-crimping can cause a diameter difference in the pre-crimped stent 1 as shown in FIG. 40, i.e., adjacent sections 10*c*, 10*d* of the stent 1 have a different diameter. This difference can be equalized, e.g., by pre-crimping again. To accomplish this, the balloon catheter 2 can be pulled a little upward in the area B, so that the stent 1 is completely enclosed by the film sheets 60 or the film sections 63. However, the diameter difference need not necessarily be equalized during pre-crimping, since the stent 1 can also be processed in the subsequent process step (repositioning and crimping) with the diameter difference.

Alternatively to the vertical insertion of the stent 1 or the balloon catheter 2 into the area B between the pressure plates 6, a horizontal processing of the stent 1 or of the balloon catheter 2 is also conceivable. Instead of a stop 7 located outside the pressure plates 6, it is also conceivable for there to be a stop 7 in the form of a plunger, which enters into the area B between the pressure plates 6 and defines the position of the stent 1 in this way (see above).

Figure 34:
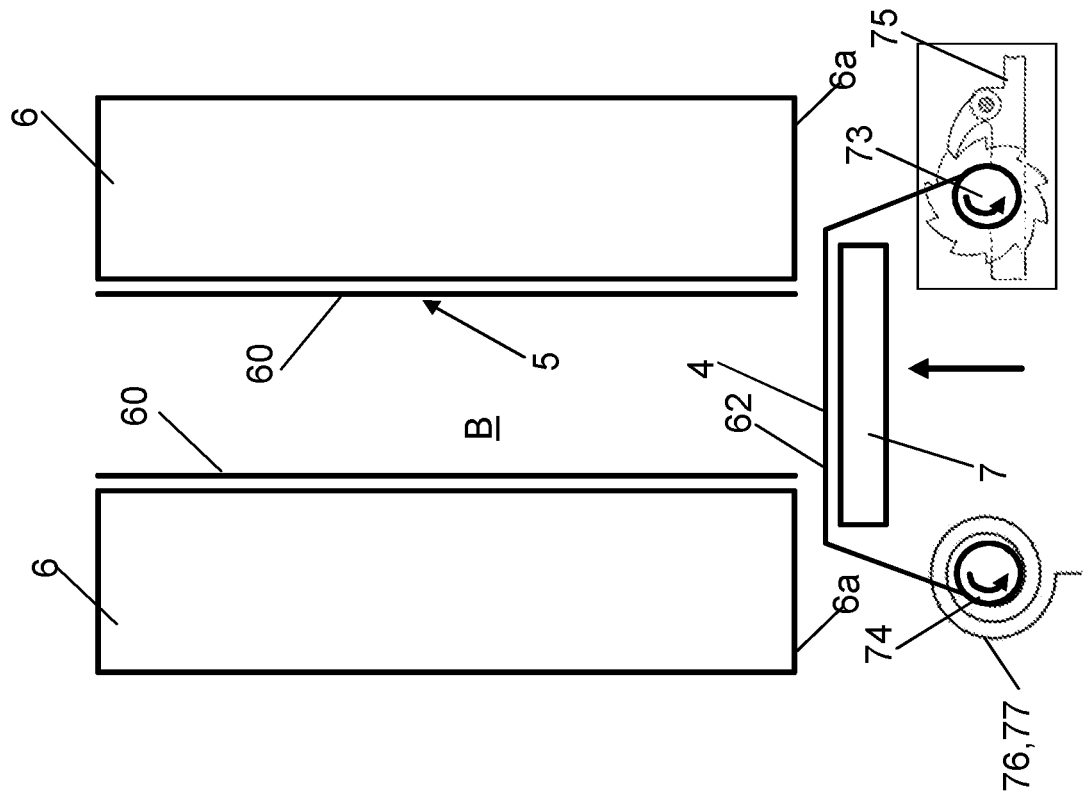
FIG. 34 an alternative detail of an embodiment of the process, wherein the stop is covered by means of a film sheet, which is unwound by the stop.

Furthermore, the advancement of the at least one film sheet 60 in the area B or of the film sheet 62 on the stop 7 can also be produced by means of the movement of the pressure plates 6 or of the mechanical stop 7, instead of by means of a motorized drive. To accomplish this, it is possible to use, e.g., a spring-ratchet system, as is shown in FIG. 34 for the stop 7. Here the film sheet 62 is unwound from a feed roller 73 and secured by means of a ratchet 75 when the stop 7 is moved to the bottoms 6*a* of the pressure plates 6. Furthermore, the film sheet 61 can be wound up on a take-up roller 74 that is acted on by means of a spring 76 and that can also be locked in place by means of a ratchet 77.

Figure 33:
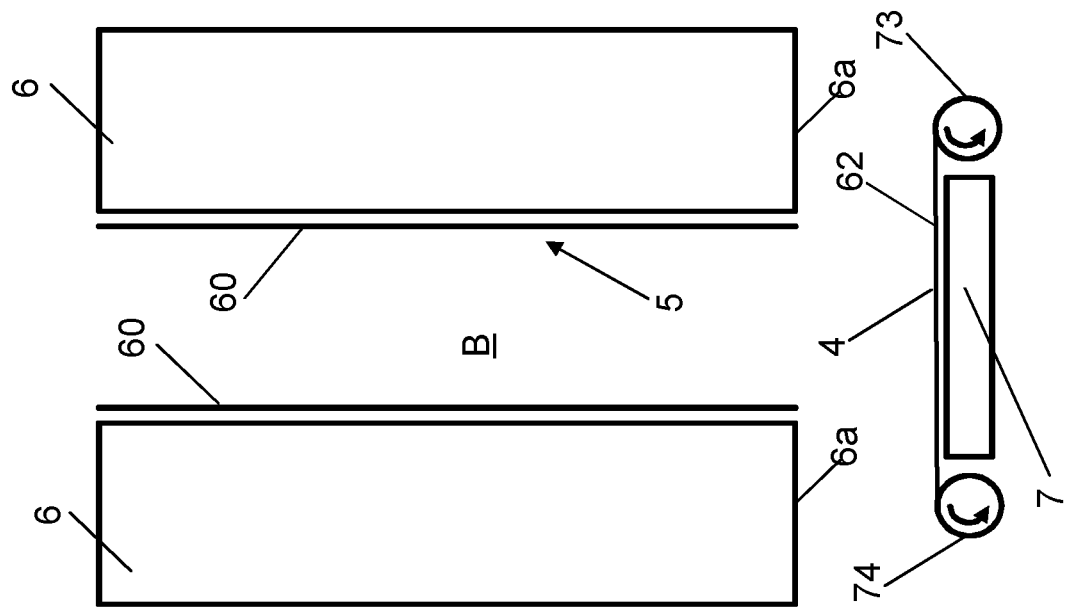
FIG. 33 a detail of an embodiment of the process, wherein the stop is covered by means of a film sheet, which is wound up by means of a driven take-up roller.

By contrast, FIG. 33 shows an embodiment in which the film sheet 61 on the stop 7 is unwound from a feed roller 73 and wound up on a driven take-up roller 74.

As before, in the case of the capsule-based or support-based protection device, the film-based protection device also allows effective prevention of cross contamination during machine pre-crimping of drug-coated stents. The film tunnel 61 produced in the process, which is preferably formed from at least three separate film sheets 60 or by at least three film sections 63 of a film sheet 60, is also advantageous for the final crimping, especially since there is no relative motion between the film and the stent 1.

The invention claimed is:

1. A process for arranging a stent on a balloon of a balloon catheter, comprising:
   a) Providing a stent having a wall structure that circles in a peripheral direction and that extends along a longitudinal axis and surrounds an interior of the stent extending along the longitudinal axis, the wall structure having an inner surface facing the interior and an outer surface facing away from the inner surface;
   b) Providing a protection device to avoid contamination of the stent;
   c) Inserting the stent in an insertion direction into an area between multiple movable pressure plates until a stop limits motion of the stent in the insertion direction, wherein the stop comprises a withdrawable stop positioned to abut the protection device;
   d) Moving the pressure plates in the direction toward the outer surface of the stent so that the stent is held by the pressure plates;

e) Inserting the balloon catheter into the interior of the stent so that the wall structure of the stent surrounds the balloon;
f) Moving the pressure plates in the direction toward the outer surface of the wall structure of the stent so that the pressure plates crimp the stent on the balloon; and
g) Opening the pressure plates and withdrawing the balloon catheter out of the area between the pressure plates with the stent crimped on the balloon; wherein
the stent is inserted into the area according to step c) such that one or both of the following occurs
at least a first part of the protection device prevents contact between a face of the stent and the stop; and
at least a second part of the protection device is located between the outer surface of the wall structure of the stent and the pressure plates when the pressure plates are pressed against the outer surface of the stent with the second part of the protection device between them, the stent being held by the pressure plates in step d) with the second part of the protection device between them, and the pressure plates crimping the stent on the balloon in step f) with the second part of the protection device between them.

2. A process according to claim 1, wherein the protection device is formed by a capsule that has at least one elastically deformable wall, the stent being arranged in the capsule before being arranged in the area so that the at least one deformable wall surrounds the outer surface of the wall structure of the stent.

3. A process for arranging a stent on a balloon of a balloon catheter, comprising:
a) Providing a stent having a wall structure that circles in a peripheral direction and that extents along a longitudinal axis and surrounds an interior of the stent extending along the longitudinal axis, the wall structure having an inner structure facing the interior and an outer surface facing away from the inner surface;
b) Providing a protection device to avoid contamination of the stent;
c) Inserting the stent in an insertion direction into an area between multiple movable pressure plated so that a stop limits motion of the stent in the insertion direction;
d) Moving the pressure plates in the direction toward the outer surface of the stent so that the stent is held by the pressure plates;
e) Inserting the balloon catheter into the interior of the stent so that the wall structure of the stent surrounds the balloon;
f) Moving the pressure plates in the direction toward the outer surface of the wall structure of the stent so that the pressure plates crimp the stent on the balloon; and
g) Opening the pressure plates and withdrawing the balloon catheter out of the area between the pressure plates with the stent crimped on the balloon; wherein
the stent is inserted into the area according to step c) such that one or both of the following occurs
at least a first part of the protection device prevents contact between a face of the stent and the stop; and
at least a second part of the protection device is located between the outer surface of the wall structure of the stent and the pressure plates when the pressure plates are pressed against the outer surface of the stent with the second part of the protection device between them, the stent being held by the pressure plates in step d) with the second part of the protection device between them, and the pressure plates crimping the stent on the balloon in step f) with the second part of the protection device between them, wherein the protection device is formed by a capsule that has at least one elastically deformable wall, the stent being arranged in the capsule before being arranged in the area so that the at least one deformable wall surrounds the outer surface of the wall structure of the stent, and wherein the capsule has a projection at one end of the capsule.

4. A process according to claim 3, wherein the projection forms an abutment for at least one of the pressure plates as the balloon catheter is withdrawn from the area between the pressure plates.

5. A process for arranging a stent on a balloon of a balloon catheter, comprising:
a) Providing a stent having a wall structure that circles in a peripheral direction and that extents along a longitudinal axis and surrounds an interior of the stent extending along the longitudinal axis, the wall structure having an inner structure facing the interior and an outer surface facing away from the inner surface;
b) Providing a protection device to avoid contamination of the stent;
c) Inserting the stent in an insertion direction into an area between multiple movable pressure plated so that a stop limits motion of the stent in the insertion direction;
d) Moving the pressure plates in the direction toward the outer surface of the stent so that the stent is held by the pressure plates;
e) Inserting the balloon catheter into the interior of the stent so that the wall structure of the stent surrounds the balloon;
f) Moving the pressure plates in the direction toward the outer surface of the wall structure of the stent so that the pressure plates crimp the stent on the balloon; and
g) Opening the pressure plates and withdrawing the balloon catheter out of the area between the pressure plates with the stent crimped on the balloon; wherein
the stent is inserted into the area according to step c) such that one or both of the following occurs
at least a first part of the protection device prevents contact between a face of the stent and the stop; and
at least a second part of the protection device is located between the outer surface of the wall structure of the stent and the pressure plates when the pressure plates are pressed against the outer surface of the stent with the second part of the protection device between them, the stent being held by the pressure plates in step d) with the second part of the protection device between them, and the pressure plates crimping the stent on the balloon in step f) with the second part of the protection device between them, wherein the first part of the protection device is formed by a support for the stent, the support having a pin that is inserted into the interior of the stent before the stent is inserted in the area between the pressure plates.

6. A process according to claim 5, wherein the support has a base from which the pin sticks out and which projects beyond the outer surface of the wall structure of the stent in such a way that the base makes contact with the stop.

7. A process according to claim 6, wherein the support has a head part that is detachably connectable with the pin and/or the base, the head part being connected with the pin and/or with the base before the stent is arranged in the area, the head part being removed from the pin after insertion of the stent into the area.

8. A process according to claim 6, wherein the pin has a spring element at an end section opposite the base.

9. A process according to claim 7, wherein the pin has a first end section and an opposite second end section, the support further having a first and a second spring element, the first spring element being arranged on the first end section and the second spring element being arranged on the second end section of the pin.

10. A process according to claim 1, wherein the second part of the protection device has a one or more flexible film sheets.

11. A process according to claim 10, wherein the one or more flexible film sheets are guided through the area between the pressure plates so that the one or more flexible film sheets form a film tunnel enclosing the outer surface of the wall structure of the stent in the peripheral direction when the pressure plates are moved in the direction toward the outer surface of the wall structure of the stent.

12. A process according to claim 11, wherein the one or more flexible film sheets are arranged so that they project beyond the pressure plates in the insertion direction.

13. A process according to claim 5, wherein the first part of the protection device has a film sheet.

14. A process according to claim 1, wherein the stent is arranged in the area so that an end section of the stent projects beyond the pressure plates in the insertion direction.

15. A process according to claim 1, wherein the stent is repositioned with respect to the balloon after crimping on the balloon and, after the repositioning, is crimped onto the balloon again, to fix the repositioned stent on the balloon.

\* \* \* \* \*